United States Patent [19]

Kadin

[11] 4,059,584

[45] Nov. 22, 1977

[54] 2-ACYLAMINO-3-[3-(DIALKYLAMINO)-PROPYL]IMIDAZO[4,5-B]PYRIDINES

[75] Inventor: Saul Bernard Kadin, New London, Conn.

[73] Assignee: Pfizer, New York, N.Y.

[21] Appl. No.: 712,225

[22] Filed: Aug. 6, 1976

Related U.S. Application Data

[62] Division of Ser. No. 495,375, Aug. 7, 1974, Pat. No. 4,002,623.

[51] Int. Cl.$^2$ .......................................... C07D 487/04
[52] U.S. Cl. .......................... 260/268 BC; 260/240 D; 260/293.55; 260/293.6; 544/127; 544/139; 542/421

[58] Field of Search ..... 260/268 BC, 240 D, 247.2 A, 260/268 BF, 293.55, 293.6

[56] References Cited

U.S. PATENT DOCUMENTS 3,004,978  10/1961  Hunger et al. .................... 260/293.6

*Primary Examiner*—Paul M. Coughlan, Jr.
*Attorney, Agent, or Firm*—Connolly and Hutz

[57] ABSTRACT

1-[3-(Dialkylamino)propyl]-2-acylaminobenzimidazoles and 2-acylamino-3-[3-(dialkylamino)propyl]-imidazo[4,5-b]pyridines and salts thereof with pharmaceutically acceptable acids, a novel class of compounds useful in the treatment of inflammatory conditions. Alternate methods of preparation are provided and the primary synthetic route is described in detail.

5 Claims, No Drawings

2-ACYLAMINO-3-[3-(DIALKYLAMINO)PROPYL]-IMIDAZO[4,5-b]PYRIDINES

CROSS-REFERENCE TO RELATED APPLICATION

This application is a division of application Ser. No. 495,375 filed Aug. 7, 1974 and now U.S. Pat. No. 4,002,623 as issued Jan. 11, 1977.

BACKGROUND OF THE INVENTION

This invention relates to various new and useful 1-[3-(dialkylamino)propyl]-2-acylaminobenzimidazoles and 2-acylamino-3-[3-(dialkylamino)propyl]imidazo[4,5-b]pyridines and pharmaceutically acceptable salts thereof and to the method of use of said agents in the inhibition of inflammation in subjects suffering from chronic inflammatory conditions.

Whereas, in the past, corticosteroids have generally been most prevalently used in the treatment of inflammator diseases and, more recently, non-steroidal anti-inflammatory agents generally of an acidic nature have been examined for their utility in the treatment of similar diseases, the present invention relates to potent and novel compounds, neither steroid-like nor acidic, which are useful in the treatment of inflammatory diseases.

SUMMARY OF THE INVENTION

In accordance with the present invention, it has now been found that compounds of the general structure, below, are surprisingly, extremely useful when employed in the treatment of chronic inflammatory conditions. More specially, the novel compounds of the invention are those having the formula:

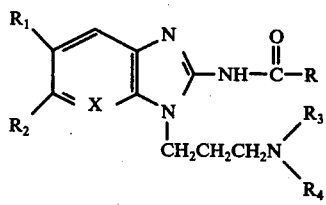

and pharmaceutically acceptable acid addition salts thereof wherein R is alkyl having from 1 to 9 carbon atoms, cyclobutyl, adamantyl, styryl, chlorostyryl, furyl, phenyl, or mono or di-substituted phenyl wherein each substituent is chloro, bromo, fluoro, trifluoromethyl, phenyl, alkoxy or alkyl said alkoxy or alkyl having from 1 to 4 carbon atoms; $R_1$ and $R_2$ are each hydrogen, chloro, bromo, fluoro, trifluoromethyl, dimethylsulfonamido, methoxy or methyl; X is carbon or nitrogen; and $R_3$ and $R_4$ when taken separately are each alkyl having from 1 to 4 carbon atoms and when taken together with the nitrogen to which they are attached form a piperidino, pyrrolidino, morpholino, piperazino, 4-benzylpiperazino or 4-alkylpiperazino ring and alkyl having from 1 to b 4 carbon atoms.

The invention also discloses a method of producing inhibition of inflammation in subjects suffering from chronic inflammatory conditions which comprises the administration of an effective amount of a compound of the above formula and salts thereof with pharmaceutically acceptable acids. An especially effective compound of this novel class of antiinflammatory agents is 1-[3-(4-methyl-1-piperazinyl)propyl]-2-(3,4-dichlorobenzamido)benzimidazole.

DETAILED DESCRIPTION OF THE INVENTION

The primary process employed for the synthesis of the novel compounds of the invention is shown in the following sequence of reactions wherein R, $R_1$, $R_2$, $R_3$, $R_4$ and X are as defined above.

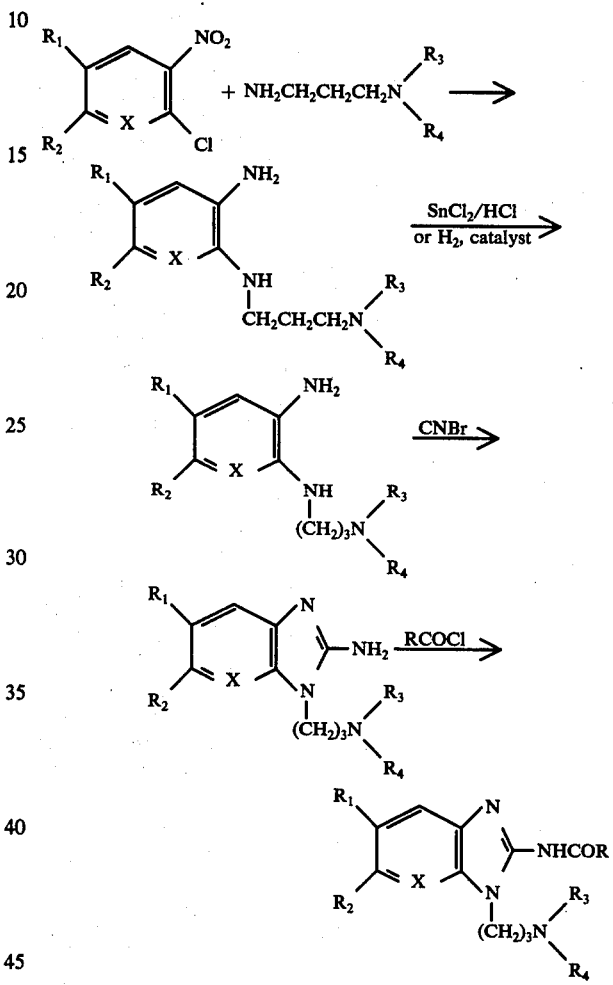

The starting materials of the general formula

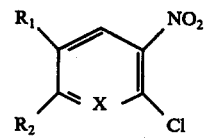

wherein $R_1$, $R_2$ and X are as previously defined are commercially available with the exception of 4-chloro-3-nitro-N,N-dimethylbenzenesulfonamide. The latter was prepared from 2-chloronitrobenzene by reaction with an excess of chlorosulfonic acid at elevated temperature until hydrogen chloride gas evolution essentially ceased. The isolated 4-chloro-3-nitrobenzenesulfonyl chloride was dissolved in methanol and reacted with dimethylamine at ice-bath temperature to obtain the desired N,N-dimethylsulfonamide. The N,N-dialkylaminopropyl amines of the structure

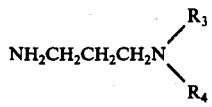

wherein $R_3$ and $R_4$ are as previously indicated, are all available commercially or may be readily prepared by catalytic reduction of the adduct of acrylonitrile and the appropriate secondary amine by the method of Whitmore, et al., *J. Am. Chem. Soc.*, 66, 725 (1944).

The reaction between the above described starting materials may be carried out in a reaction inert solvent if so desired. However, in many cases it is more convenient to perform the reaction in the absence of solvent. When solvents ae employed, they should be capable of readily dissolving both reactants, and be of sufficiently high boiling point to allow the reaction to be carried out at reflux temperature or below in reasonably short time. Reaction times of about one to 24 hours at temperatures in the range of about 60° to 160° C. are usually adequate. However, the usual time and temperature relationship common to all chemical reactions prevails such that the reaction may be carried out in less time at higher temperatures and, conversely, at lower temperature over a longer time with substantially similar results. Benzene, toluene, xylene, ethanol and isopropanol are typical of the solvents employed. The reaction may be carried out in the presence of equimolar amounts of the two reactants of an excess of either one. However, for reasons of economy, an excess of the 3-dialkylamino propylamine is ordinarily employed to force the reaction toward completion by binding the hydrogen chloride generated in the reaction. This function of removing HCl from the equilibrium may be accomplished by introduction of a base such as an alkali metal carbonate or bicarbonate. The products are isolated by standard methods. For example, the reaction mixture is poured into excess of an aqueous acid such as hydrochloric acid, the aqueous phase made alkaline and the product (free base) extracted into an organic solvent from which it may be isolated by evaporation of solvent. Alternatively, the product may be isolated in the salt form by introduction of the appropriate acid (e.g. anhydrous HCl) into the solution in organic solvent.

The products isolated from the first step of the primary reaction sequence are 2-[3-(N,N-dialkylamino)-propylamino]nitrobenzenes or the corresponding -3-nitropyridines of the general structure:

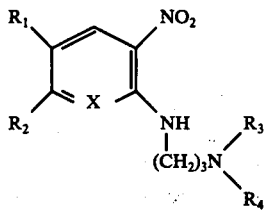

wherein $R_1$, $R_2$, $R_3$, $R_4$ and X are as previously indicated. In the second step of this reaction sequence, the aromatic nitro group is reduced to a primary amine function by methods which seek to minimize possible side reactions. This is accomplished by utilizing stannous chloride in concentrated hydrochloric acid or by catalytic hydrogenation with a palladium catalyst. Both methods afford excellent yields of the desired products. In the former method, mole ratios of stannous chloride to nitro group containing compound of 1.5:1 to 6:1 may be employed. However, mole ratios of 2:1 to 4:1 are preferred. The reaction is carried out in an excess of concentrated hydrochloric acid. It is preferably done under an atmosphere of inert gas such as nitrogen or argon. The aromatic nitro compound, preferably dissolved or dispersed in concentrated hydrochloric acid. is added to a mixture of stannous chloride and concentrated hydrochloric acid over a period of about 0.5 to 5 hours at temperatures of from about 25° to 75° C. and preferably about 1 to 3 hours at about 40° to 60° C. During said addition, the reaction is usually exothermic. Consequently, the addition rate can be set so that it maintains the reaction within the desired temperature range. After the addition is complete, the reaction mixture is maintained at a temperature in the range of about 20° to 100° C. and preferably about 40° to 80° C. for about 1 to 30 hours or until the reaction is substantially complete. The extent to which the reaction has progressed toward completion may be estimated by thin-layer chromatography on silica gel employing a solvent system capable of resolving starting material and product. Examples of such solvent systems are 10% diethylamine in ethyl acetate and 5% diethylamine in tetrahydrofuran. The product is isolated by standard techniques usually involving filtration of the cooled reaction mixture to remove the product from the reaction mixture as a crude hydrochloride salt. The salt is then made alkaline and the free base extracted into an organic solvent such as chloroform or methylene chloride from which the N-substituted o-phenylenediamines or corresponding pyridine compounds (X is nitrogen) are isolated. They may be further purified by crystallization, distillation or a combination thereof. The same products, of the general structure.

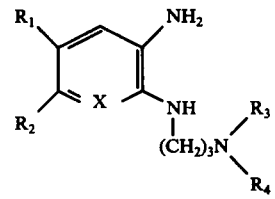

wherein $R_1$, $R_2$, $R_3$, $R_4$ and X are as defined above may also be obtained from the same aromatic nitro compounds in each case, by catalytic hydrogenation using palladium or other suitable noble metal or transition metal catalyst. The catalyst of choice is palladium on carbon in which the palladium content is in the range of about 2 to 20 percent by weight and preferably 5–10% by weight. The hydrogenation is carried out under elevated pressure in conventional hydrogenation equipment. A reaction-inert solvent such as the lower alkanols can be used as diluent. The theoretical amount of hydrogen, 3 moles per mole nitro group containing compound, is taken up over about 1 to 4 hours at temperatures of about 20° to 50° C. The product is isolated by evaporation of solvent after filtering off the catalyst. The products so obtained are ordinarily sufficiently pure for use in the next step. They may be purified, if desired, by recrystallization, distillation or other conventional means.

Ring closure is effected by reaction of the products obtained in the preceding reaction with cyanogen bromide in aqueous or aqueous-alkanol media to afford 2-aminobenzimidazoles and 2-amino-imidazo[4,5-b]pyridines of the structure

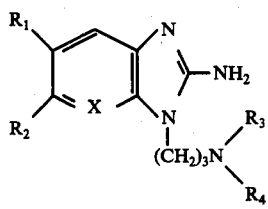

in which $R_1$, $R_2$, $R_3$, $R_4$ and X are as previously defined. When an aqueous alkanolic solvent system is employed, the lower alkanols having four carbons or less are used. Ethanol and isopropanol are especially preferred. The reaction is ordinarily carried out with an excess of cyanogen bromide of about 1.1 to 5 moles per mole of O-diamine starting material. The reaction is preferably carried out in an inert atmosphere. The cyanogen bromide addition rate may be controlled in order to regulate the temperature since the reaction is exothermic in many instances. The cyanogen bromide is added to the mixture of o-diamine starting material and solvent at a reaction temperature which may range from ambient temperature to about 80° C. and preferably 40° to 70° C. The addition is completed in typical examples in about 0.5 to 2 hours, after which the reaction may be continued, if required, for periods up to 24 hours to insure completion of the reaction. Product isolation and purification entails extraction of the basified reaction mixture with an organic solvent such as chloroform, methylene chloride, ethyl ether and the like and purification of the isolated product by crystallization or column chromatography if required. Alternatively, the product may be isolated as a salt by reacting a solution in an appropriate organic solvent with an essentially anhydrous acid such as HCl, HBr and $CH_3SO_3H$.

The final step of the primary reaction sequence employed to obtain the products of the invention involves acylation of the 2-amino substituent of the products of the preceding reaction step. Said acylation has been carried out in most instances with acid chlorides; and in the remaining cases with carboxylic acid anhydrides. As those skilled in the art will readily recognize, other reagents might also be employed with equal facility for said acylation. Examples of other such reagents include mixed anhydrides, lower alkyl esters of carboxylic acids, lactones and ketenes.

The acid chlorides, RCOCl and anhydrides,

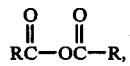

wherein R is as previously defined for the products of the invention, are either available commercially as reagent grade chemicals, or are readily prepared from the corresponding carboxylic acids by standard procedures well known in the art. The acylation of the 2-aminobenzimidazoles and 2-amino-imidazo[4,5-b]pyridine starting materials with acid chlorides or acid anhydrides, is normally carried out in an organic solvent such as chloroform, methylene chloride, pyridine, hexamethylphosphoric triamide, and the like.

Certain bases are optionally added to the reaction mixture in order to bind by-product acids. Said by-products acids are hydrogen chloride, when an acid chloride is used as acylating agent, and RCOOH, wherein R is a previously defined, when an acid anhydride is employed. Typical examples of such bases that do not react with the acylating agent under the conditions of the reaction, but readily react with by-product acids to form salts, are potassium carbonate and triethylamine. The use of such a base spares unreacted starting material from being removed from the equilibrium via salt formation. The molar ratio of starting material to acylating agent employed may vary from about 1:1 to 1:2. The acylating agent is usually added slowly to a solution or slurry of starting material, optionally containing an aforementioned base, at temperatures in the range of about 0° to 80° C., and preferably about 10° to 60° C. Following the addition, the reaction mixture is maintained at the temperature of the addition for a short time, then stirred at ambient temperature for periods up to about 24 hours to ensure completion of the reaction. The product may then be isolated as the free base or in the form of an acid addition salt. Ordinarily, the reaction mixture is partitioned between aqueous alkali and solvent. The solvent phase may be dried and evaporated to afford the product in the free base form or, alternatively, be subjected to treatment with a suitable acid to obtain acid addition salts of the novel compounds of the invention. Such conversions are best carried out as rapidly as possible, and under conditions dictated by the stability of reactants. The salts thus formed may be utilized as such for their chemotherapeutic activity or may be purified further. Such salts may also be used for regeneration of the free base form. The purified free base, thu obtained, may be reconverted to the same or a different acid addition salt, if so desired.

Examples of acids which will form pharmaceutically acceptable addition salts with free base forms of the products of the invention are hydrochloric, hydrobromic, hydroiodic, nitric, sulfuric, sulfurous, phosphoric, methanesulfonic, acetic, lactic, citric, malic, tartaric, succinic, maleic, fumaric, and gluconic acids.

Another method for preparing 1-[3-(dialkylamino)-propyl]-2-aminobenzimidazoles and 2-amino-3-[3-(dialkylamino)propyl]imidazo[4,5-b]pyridines is by alkylation of the corresponding 2-aminobenzimidazole or 2-aminoimidazo[4,5-b]-pyridine with a 1-(N,N-dialkylamino)-3-bromopropane prepared as described by Kreisel and Gisvold, J. Pharm. Sci., 56, 325 (1967) and McElvain and Bannister, J. Am. Chem. Soc., 76, 1126 (1954). This method is outlined below. $R_1$, $R_2$, $R_3$, $R_4$ and X are as previously defined.

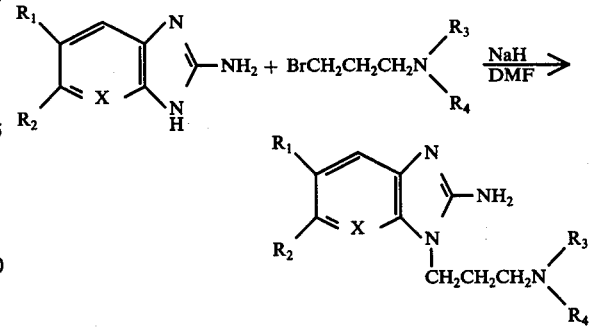

The compound to be alkylated and sodium hydride equivalent to the theoretical amount of by-product acid generated in the reaction are combined in dimethylformamide as solvent. The alkyl bromide is added to the mixture at a temperature in the range of about −10° to 50° C., after which the reaction is allowed to proceed to substantial completion. The isolated products can then be acylated as described above to provide the compounds of the invention. This method is preferable over the primary synthetic method in certain instances, as for example, in the case where R₁ and R₂ are both chloro. The preparation of 5-chloro-2-aminobenzimidazole by chlorination of 2-aminobenzimidazole with hydrochloric acid and hydrogen peroxide has been described by Leonard et al., *J. Am. Chem. Soc.*, 69, 2459 (1947). It has now been found that 5,6-dichloro-2-aminobenzimidazole is obtained in excellent yield when twice the amount of peroxide is employed, i.e.,

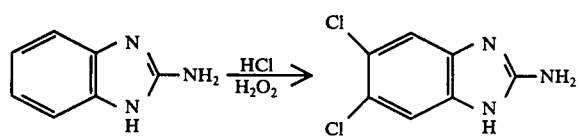

The 5,6-dichloro compound is readily alkylated as described above.

H. Reimlinger, *Chem. Ber.*, 104, 2801 (1971) has described the use of benzoyl imidocarbonyl chloride (C₆H₅CON=CCl₂, N-dichloromethylene benzamide, benzoyl cyandichloride) to cyclize amidines to oxo-s-triazines, and amidrazones to 3-benzoyl amino-1,2,4-triazoles, Synthesis, 1970, 433. It has now been found that imidocarbonyl chlorides, RCON=CCl₂, and structurally related reagents in which the chloride atoms are replaced by equally facile leaving groups provide still other methods for preparation of the instant compounds of this invention. This is illustrated by the following general reaction wherein R, R₁, R₂, R₃, R₄ and X are as defined above, and Y and Y' when taken separately are each chlorine, bromine, alkoxy and alkythio having up to four carbon atoms and when taken together is sulfur.

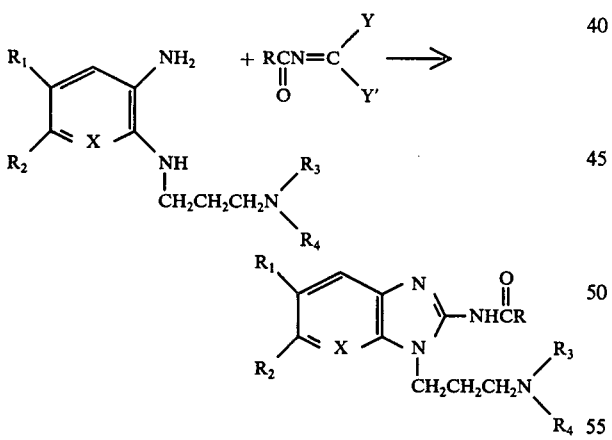

The reagent,

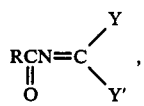

wherein R, Y and Y' are as defined above, is added to the above depicted o-phenylenediamine or corresponding pyridine analog preferably dissolved in a reaction inert solvent such as benzene, toluene, ethyl acetate, ethanol, isopropanol, acetone or tetrahydrofuran. The reaction is carried out at temperatures in the range of about 0° to 100° C. and preferably at about 20°-70° C. Equimolar amounts of reactants ordinarily afford adequate yields of the desired products; however, an excess of either one may be employed if so desired. The resulting reaction mixture may then be maintained at room temperature for periods up to 24 hours or until the reaction is substantially complete. The product is isolated and purified by standard techniques.

Additional methods of preparation of the novel compounds of the invention are based on the use of S-alkyl-1,3-diacylisothioureas which are prepared by acylation of S-alkyl isothioureas wherein alkyl substituents having up to four carbon atoms and especially methyl are preferred. These reagents are employed as outlined below to provide the desired products.

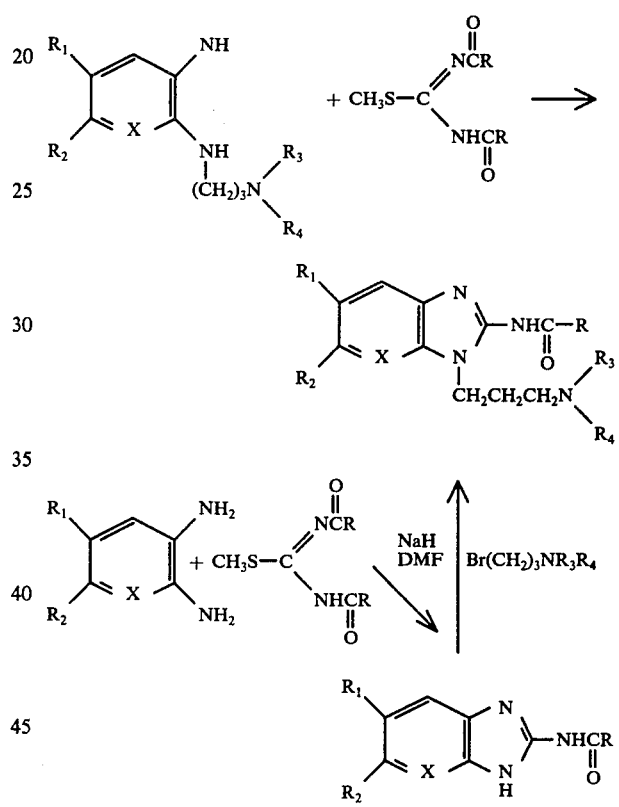

The acylation of S-alkyl isothioureas is preferably carried out using acid chlorides in aqueous solution at temperatures of about 0° to 50° C. The hydrogen chloride evolved is neutralized by periodic addition of base. The cyclization steps, illustrated above, may be carried out in the absence of solvent or in a polar, aprotic solvent such as dimethylformamide, dimethylsulfoxide, or hexamethylphosphorictriamide. While temperatures in the range of about 100° to 200° C. may be employed, the reaction is preferably carried out at about 120° to 160° C. When the primary o-phenylenediamines or 2,3-diaminopyridines are used as starting material for this reaction, the 2-acylaminobenzimidazoles and the corresponding imidazo[4,5-b]pyridines thus obtained are alkylated, as described above, with a 1-(N,N-dialkylamino)-3-bromopropane and sodium hydride to obtain the compounds of the invention.

The adjuvant arthritis test described by Walz et al., *Ann. Rheum. Dis.*, 30, 303 (1971) was selected as the method of choice for the determination of the extent to which the novel compounds of the present invention are therapeutically effective as anti-inflammatory agents. Adjuvant arthritis is a crippling deformity in rats resulting from diffuse connective tissue involvement. It is considered by some authorities to be the best available experimental animal model of human rheumatoid arthritis because of its strong clinical and pathological similarities to the human disease and because it can be effectively treated with known anti-arthritic drugs. In this test, lesions resembling those of human rheumatoid arthritis are induced by the injection of complete Freund's adjuvant into one hind leg of a rat. A vigorous inflammatory response occurs in the injected hind leg and reaches its greatest size in about 4 days. This primary response is followed by the development of a second inflammatory response, appearing about 12-16 days post-injection, that occurs in the uninjected hind leg. While the compounds of the injection are capable of inhibiting the degree of inflammation in both legs, the inhibition of swelling in the uninjected led at 16 days is considered to be more meaningful measure of antiarthritic activity.

As previously indicated, the 1-[3-(dialkylamino)propyl]-2- acylaminobenzimidazoles and 2-acylamino-3[3-(dialkylamino)propyl]imidazo[4,5-b]pyridines of the present invention are therapeutically effective as anti-inflammatory agents in mammals. The following compounds, and pharmaceutically acceptable acid addition salts thereof, are outstandingly effective in this regard.

1-[3-(N-morpholino)propyl]-2-(3-chlorobenzamido)benzimidazole,
1-[3-(4-methyl-1-piperazinyl)propyl]-2-(3,4-dichlorobenzamido)benzimidazole,
1-[3-(4-methyl-1-piperazinyl)propyl]-2-(2-furamido)benzimidazole,
1-[3-(4-methyl-1-piperazinyl)propyl]-2-n-decanamido)benzimidazole,
1-[3-(4-methyl-1-piperazinyl)propyl]-2-benzamido-5,6-dimethylbenzimidazole,
1-[3-(4-methyl-1-piperazinyl)propyl]-2-(3-chlorobenzamido)-5-(N,N-dimethylsulfonamido)benzimidazole,
1-[3-(4-methyl-1-piperazinyl)propyl]-2-(3-methoxybenzamido)-6-methylbenzimidazole,
1-[3-(4-methyl-1-piperazinyl) propyl]-2-(3-trifluoromethylbenzamido)-5-trifluoromethylbenzimidazole,
1-[3-(4-methyl-1-piperazinyl)propyl]-2-(4-trifluoromethylbenzamido)-5-trifluoromethylbenzimidazole,
1-[3-(4-methyl-1-piperazinyl)propyl]-2-(3-chlorobenzamido)-5-trifluoromethylbenzimidazole,
1-[3-(4-methyl-1-piperazinyl)propyl]-2-(3-methoxybenzamido)-5-methylbenzimidazole,
1-[3-(4-methyl-1-piperazinyl)propyl]-2-(p-chlorocinnamido)-5-methylbenzimidazole,
1-[3-(4-methyl-1-piperazinyl)propyl]-2-(3,4-dichlorobenzamido)-5-methoxybenzimidazole,
1-[3-(4-methyl-1-piperazinyl)propyl]-2-(4-trifuoromethylbenzamido)-5-chlorobenzimidazole,
1-[3-(1-piperidino)propyl]-2-(4-trifluoromethylbenzamido)benzimidazole,
1-[3-(dimethylamino)propyl]-2-(4-chlorobenzamido)benzimidazole,
1-[3-(dimethylamino)propyl]-2-(4-methoxybenzamido)benzimidazole,
2-(3-trifluoromethylbenzamido)-3-[4-(methyl-1-piperazino)propyl]imidazo[4,5-b]pyridine,
2-(3,4-dichlorobenzamido)-3-[4-(methyl-1-piperazino)propyl]imidazo[4,5-b]pyridine.

Additionally, none of the above compounds cause any substantial side effects to occur in the subjects to whom they are so administered, i.e., no problems of toxicity or of a harmful pharmacological nature, either gross or microscopic, are encountered when said compounds are administered for the aforestated purposes in the prescribed manner. Of the above-mentioned compounds 1-[3-(4-methyl-1-piperazinyl)propyl]-2-(3,4-dichlorobenzamido)benzimidazole and its pharmaceutically acceptable salts are especially preferred.

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally, for example, intramuscularly or subcutaneously. For parenteral administration, they are best used in the form of a sterile aqueous solution which may contain other solutes, for example, enough salts or glucose to make the solution isotonic.

With respect to dosage levels, a broad dosage range of 10 to 1500 mg. for adults is appropriate, a particularly preferred range being 100 to 500 mg., such dosage being administrable up to four times a day. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

The invention is illustrated by the following Examples.

EXAMPLE 1

1-[2-(4-Methyl-1-piperazinyl)propyl]-2-aminobenzimidazole

To a mechanically stirred solution of o-chloronitrobenzene (248 g., 1.57 mole) in 1000 ml. xylene, under nitrogen, was added 1-(3-aminopropyl)-4-methylpiperazine (373 g., 2.36 mole). The resultant dark yellow solution was then refluxed for 1.3 hrs. at which time a heavy yellow orange precipitate formed. Continued refluxing (16 hours) gave a brown suspension. The reaction mixture was cooled to 5° C. and 600 ml. of 6N HCl was added. Following separation of the organic layer the aqueous phase was cooled, made basic (pH 9) with 50% KOH, and extracted with chloroform (4 × 500 ml.). The combined organic layers were dried (MgSO$_4$) and evaporated in vacuo yielding 454.1 g. of 2-[3-(4-methyl-1-piperazinyl)propylamino]nitrobenzene as a dark red oil (theory 438 g.). A small sample of the oil was converted to the corresponding hydrochloride which on recrystallization from ethanol gave an analytical sample, m.p. 263°–265° C.

Anal Calc'd for C$_{14}$H$_{22}$O$_2$N$_4$·2HCl: C, 47.91; H, 6.89; N, 15.96. Found: C, 47.74; H, 6.88; N, 15.83.

To a mechanically stirred solution of stannous chloride (1060 g., 4.71 mole) in concentrated hydrochloric acid (1200 ml.), under nitrogen, was added a solution of 2-[3-(4-methyl-1-piperazinyl)propylamino]nitrobenzene (438 g., 1.57 mole) in conc. HCl (800 ml.) at a rate sufficient to maintain the reaction temperature at 55°–60° C. The addition took place over about 1.5 hours. The heavy white precipitate which formed during the course of the addition, was stirred for an additional 1 hour. The reaction mixture was then filtered and the resultant white solid was dissolved in 3 liters of water. An equal volume of chloroform was added, the mixture was cooled to 5° C. and adjusted to pH 10, with 50% KOH. The organic layer was separated, and the cold basic aqueous phase extracted again with chloroform (1l). The organic layers were combined, dried (MgSO$_4$) and evaporated in vacuo to give 334.8 g. of N-[3-(4-methyl-1-piperazinyl)propyl]-o-phenylenediamine as a brown oil (yield 97%). A small amount of the oil was triturated with hexane. The hexane layer was cooled to 5° C. forming a tan solid which on recrystallization from benzene-hexane give an analytical sample, m.p. 65°–67° C.

Anal. Calc'd for $C_{14}H_{24}N_4 \cdot \frac{1}{2}H_2O$: C, 66.20; H, 9.92; N, 22.06. Found: C, 66.02; H, 9.78; N, 21.87.

To a stirred solution of N-[3-(4-methyl-1-piperazinyl)propyl]-o-phenylendiamine (334.8 g., 1.35 mole) in water (1400 ml.) under nitrogen, was added cyanogen bromide (200 g., 1.89 mole) at a rate sufficient to maintain the reaction temperature at 50°–65° C. The addition took place over a 2 hour period. The reaction mixture was then cooled and the pH adjusted to 10 by the dropwise addition of 50% KOH. The basic aqueous layer was extracted from chloroform (5 × 500 ml.). The organic layers were combined, dried (MgSO$_4$), and evaporated in vacuo to give a dark brown semi-solid. Slurrying with acetone (300 ml.) gave on filtration and washing with acetone 120.1 g., (32.5% yield) of 1-[3-(4-methyl-1-piperazinyl)propyl]-2-aminobenzimidazole as a pale yellow solid, m.p. 195°–197° C.

Anal. Calc'd for $C_{15}H_{23}N_5$: C, 65.90; H, 8.48; N, 25.65. Found: C, 65.76; H, 8.45; N, 25.95.

EXAMPLE 2

1-[3-(4-Methyl-1-piperazinyl)propyl]-2-amino-5-chlorobenzimidazole

A mixture of 2,5-dichloronitrobenzene (95.5 g., 0.497 mole) and 1-(3-aminopropyl)-4-methylpiperazine (82.2 g., 0.522 mole) was heated in a nitrogen atmosphere at 130° C. for 5 hours and cooled to room temperature. The mixture was poured into a separatory funnel containing 1500 ml. of 3N HCl and 500 ml. chloroform. After shaking and separation of layers, the chloroform was withdrawn and the aqueous layer extracted with fresh CHCl$_3$. The aqueous layer was made alkaline with 20% NaOH and the resulting oil extracted with 3 × 600 ml. CHCl$_3$. The combined extracts were dried over Na$_2$SO$_4$ and the solvent evaporated at reduced pressure to give 131.5 g. (85% yield) of 2-[3-(4-methyl-1-piperazinyl)propylamino]-5-chloronitrobenzene as a dark orange oil.

The above product (131.5 g., 0.42 mole) was dissolved in 800 ml. of concentrated hydrochloric acid and added slowly to a solution of stannous chloride dihydrate (290 g., 1.29 mole) in 700 ml. conc. HCl. The temperature of the reaction was controlled at 50° C. by regulation of the addition rate. Total addition time was 90 minutes. After heating for an additional hour, the resulting yellow-orange thick suspension was stirred while allowing it to cool overnight. The mixture was cooled to about 10° C., filtered with suction, the cake washed with 500 ml. of cold conc. HCl, and pressed dry. The product was dissolved in 3 liters of water and NH$_4$OH added until the solution was strongly alkaline. The creamy mixture was extracted with 3 × 1000 ml. methylene chloride, the extracts were combined and washed with 1000 ml. water. The organic layer was dried (Na$_2$SO$_4$) and evaporated to dryness to obtain 98.2 g. (83% yield) of 2-[3-(4-methyl-1-piperazinyl)propylamino]-5-chloroaniline, m.p. 88°–90° C. upon recrystallization from isopropyl ether.

Anal. Calc'd for $C_{14}H_{23}N_4Cl$: C, 59.46; H, 8.20; N, 19.81. Found: C, 59.37; H, 8.17; N, 19.75.

To a solution of 2-[3-(4-methyl-1-piperazinyl)propylamino]-5-chloroaniline (70 g., 0.248 mole) in 350 ml. of water and 150 ml. ethanol was added, with stirring, 59.0 g. (0.557 mole) of cyanogen bromide in portions over 1 hour. The temperature was maintained at 40°–50° C. After the addition was completed the mixture was allowed to cool to room temperature and stirred overnight. After pouring into 1500 ml. ice water and making strongly alkaline with 20% NaOH, the precipitated solid was collected on a Buchner funnel, washed with water and dried in the vacuum oven to obtain 45.0 g. (59% yield) of crude 1-[3-(4-methyl-1-piperazinyl)propyl]-2-amino-5-chlorobenzimidazole, m.p. 223°–227° C. A portion was recrystallized from acetone as colorless needles, m.p. 228°–229.5° C.

Anal. Calc'd for $C_{15}H_{22}N_5Cl$: C, 58.35; H, 7.21; N, 22.75. Found: C, 58.35; H, 7.15; N, 22.74.

EXAMPLE 3

Following the above procedures, but starting with the appropriately substituted 2-chloronitrobenzene in each case, the following 1-[3-(4-methyl-1-piperazinyl)propyl]-2-aminobenzimidazoles were prepared.

| $R_1$ | $R_2$ | M.P., ° C. |
|---|---|---|
| CF$_3$ | H | 224–225 |
| CH$_3$ | H | 235–237 |
| OCH$_3$ | H | 201–203 |
| H | CH$_3$ | 211–212.5 |
| SO$_2$N(CH$_3$)$_2$ | H | 235–238 |

EXAMPLE 4

2-Amino-5,6-dimethylbenzimidazole (21.1 g., 0.131 mole) was dissolved in 450 ml. dimethylformamide. Then 16.6 g. (0.393 mole) of a 57% oil dispersion of sodium hydride was added in portions. After hydrogen evolution subsided 4-methyl-1-piperazinyl propyl bromide dihydrobromide (50 g., 0.131 mole), obtained by the method of Kriesel and Gisvold, *J. Pharm. Sci.*, 56, 325 (1967) was added to the ice-water cooled reaction mixture in portions over one hour. The resulting mixture was stirred for 30 minutes, then poured onto one liter of crushed ice, stirred for 15 minutes and the precipitated solid collected on a filter funnel. After drying overnight in a vacuum oven at 60° C., the product amounted to 26 g. A second crop was obtained from the mother-liquor by extraction with chloroform (4 × 1000 ml.) and concentrating the extracts to a small volume. The combined crops were dissolved in hot ethanol, carbon treated, filtered and allowed to cool slowly to obtain 15.6 g. of 1-[3-(4-methyl-1-piperazinyl)propyl]-2-amino-5,6-dimethylbenzimidazole, m.p 225.5°-227° C. A second crop, 7.1 g., m.p. 223°-225° C., was obtained by concentration of the mother-liquor. Total yield, 58%.

EXAMPLE 5

5,6-Dichloro-2-aminobenzimidazole was prepared by a modification of the method of N. J. Leonard et al., *J. Am. Chem. Soc.*, 69, 2459 (1947) for 2-amino-5-chlorobenzimidazole.

To 77.2 g. (0.58 mole) of 2-aminobenzimidazole dissolved in 500 ml. of water and 50 ml. of 12N hydrochloric acid was added an additional 900 ml. of concentrated hydrochloric acid. The solution was stirred during the addition of 120 ml. of 30% hydrogen peroxide (sp.gr. 1.10) and for 2 hours following the addition. After evaporation to dryness at reduced pressure, the residual solid was taken up in 500 ml. of water and made alkaline by addition of conc. $NH_4OH$. After the solution had been boiled it was cooled to 20° C., the precipitated solid was collected by filtration and washed with water to afford 104.5 g. (89% yield) of crude product. Upon recrystallization from ethanol it melted at 252°-254° C.

Alkylation of 2-amino-5,6-dichlorobenzimidazole with 4-methyl-1-piperazinyl propyl bromide and sodium hydride in dimethylformamide by the procedure of Example 4 gave 1-[3-(4-methyl-1-piperazinyl)-propyl]-2-amino-5,6-dichlorobenzimidazole, m.p. 226°-228° C.

EXAMPLE 6

1-[3-(4-Methyl-1-piperazinyl)propyl]-2-(3,4-dichlorobenzamido) benzimidazole dimesylate To a mechanically stirred suspension of 1-[3-(4-methyl-1-piperazinyl)propyl]-2-aminobenzimidazole (123 g., 0.45 mole) and anhydrous potassium carbonate (182 g., 1.35 mole), in methylene chloride (110 ml.) under nitrogen at 0° C. (ice-salt bath), was added 3,4-dichlorobenzoylchloride (113 g., 0.54 mole) at a rate sufficient to maintain the reaction temperature at 0°-3° C. The total time required for the addition was 1 hour. After stirring for 5 hours at ambient temperature, the reaction mixture was cooled to 10° C. and adjusted to pH 2 by the addition of 1N HCl. The precipitated hydrochloride salt was collected by suction filtration and then partitioned between 10% aqueous NaOH (800 ml.) and chloroform (1000 ml.). The phases were separated and the basic aqueous layer was extracted with chloroform (500 ml.). The organic layers were combined, dried ($MgSO_4$), and evaporated in vacuo giving 1-[3-(4-methyl-1-piperazinyl)propyl]-2-(3,4-dichlorobenzamido)benzimidazole as a pale yellow solid, m.p. 170°-172° C. Treatment with 2 equivalents of methane sulfonic acid in chloroform (500 ml.), removal of solvent and recrystallization from 1-propanol gave 136 g., (47% yield) of 1-[3-(4-methyl-1-piperazinyl)propyl]-2-(3,4-dichlorobenzamido) benzimidazole dimesylate as a white crystalline solid, m.p. 170°-173° C.

Anal. Calc'd for $C_{22}H_{25}ON_5Cl_2 \cdot 2CH_3SO_2H$: C, 45.11; H, 5.21; N, 10.96. Found: C, 44.83; H, 5.29; N, 10.66.

EXAMPLE 7

Employing the procedures described in the previous examples, the following 2-amidobenzimidazoles of the general structure I were prepared. The acylation step was carried out in each case with either the appropriate acyl chloride or acid anhydride.

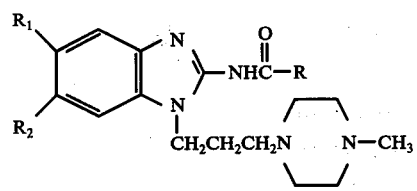

| R | $R_1$ | $R_2$ | Empirical Formula | m.p., ° C. | C | H | N |
|---|---|---|---|---|---|---|---|
| 3-Fluorophenyl | H | H | $C_{22}H_{26}ON_5F$ | 155-157 | (66.82 66.44 | 6.63 6.51 | 17.70) 17.60 |
| 3-Trifluoromethylphenyl | H | H | $C_{23}H_{26}ON_5F$ | 137-138 | (62.02 61.62 | 5.88 5.86 | 15.71) 15.74 |
| 3-Methoxyphenyl | H | H | $C_{23}H_{29}O_2N_5 \cdot 2HCl \cdot 2H_2O$ | 187-190 (dec.) | (53.49 53.46 | 6.83 6.66 | 13.55) 13.41 |
| 3-Chlorophenyl | H | H | $C_{22}H_{26}ON_5Cl \cdot \frac{1}{2}H_2O$ | 146-148 | (62.33 62.17 | 6.49 6.28 | 16.51) 16.52 |
| 3-Methylphenyl | H | H | $C_{23}H_{29}ON_5$ | 112-114 | (70.57 70.28 | 7.47 7.35 | 17.88) 18.21 |
| 3,4-Dichlorophenyl | H | H | $C_{22}H_{25}ON_5Cl_2 \cdot \frac{1}{2}H_2O$ | 170-172 | (58.67 58.86 | 5.29 5.66 | 15.54) 15.50 |
| 4-Chlorophenyl | H | H | $C_{22}H_{26}ON_5Cl \cdot \frac{1}{2}H_2O$ | 190-192 | (63.46 63.31 | 6.41 6.28 | 16.81) 16.78 |
| 4-Methoxyphenyl | H | H | $C_{23}H_{29}O_2N_5$ | 145-147 | (67.79 67.49 | 7.17 7.11 | 17.18) 17.04 |
| 4-Trifluoromethylphenyl | H | H | $C_{23}H_{26}ON_5F_3$ | 174-175 | (62.02 61.64 | 5.88 5.84 | 15.71) 15.60 |
| $CH_3(CH_2)_8-$ | H | H | $C_{25}H_{41}ON_5 \cdot 3HCl \cdot 2H_2O$ | 130 (dec.) | (52.40 52.38 | 8.44 8.13 | 12.16) 12.06 |
| 3,5-bis-Trifluoromethylphenyl | H | H | $C_{24}H_{25}ON_5F_6 \cdot 2HCl \cdot \frac{1}{2}H_2O$ | 265 (dec.) | (48.41 48.39 | 4.74 4.47 | 11.76) 11.86 |
| 1-Adamantyl | H | H | $C_{26}H_{37}ON_5 \cdot 3HCl$ | 225-227 | (57.16 57.07 | 7.35 7.28 | 12.88) 12.68 |
| 4-Phenylphenyl | H | H | $C_{28}H_{31}ON_5$ | 145-147 | (74.15 73.82 | 6.89 6.85 | 15.43) 15.43 |
| 2-Furyl | H | H | $C_{20}H_{25}O_2N_5$ | 153-155 | (65.38 64.82 | 6.86 6.75 | 19.05) 18.97 |
| Cyclobutyl | H | H | $C_{20}H_{29}ON_5 \cdot 3HCl$ | 264-266 | (51.68 51.28 | 6.94 6.90 | 15.06) 14.68 |

-continued

| R | $R_1$ | $R_2$ | Empirical Formula | m.p., °C. | C | H | N |
|---|---|---|---|---|---|---|---|
| 4-tert-Butylphenyl | H | H | $C_{26}H_{35}ON_5 \cdot 3HCl \cdot 2H_2O$ | 242–245 | (53.90<br>54.15 | 7.31<br>6.80 | 12.09)<br>11.99 |
| 3,5-Dichlorophenyl | H | H | $C_{22}H_{25}ON_5Cl_2$ | 135–136 | (59.20<br>59.27 | 5.65<br>5.60 | 15.68)<br>15.47 |
| Styryl | H | H | $C_{24}H_{29}ON_5$ | 121–123 | (71.43<br>71.53 | 7.24<br>7.24 | 17.36)<br>17.03 |
| 3-Trifluoromethylphenyl | Cl | Cl | $C_{23}H_{24}ON_5Cl_2F_3 \cdot 2HCl \cdot \frac{1}{2}H_2O$ | 297 (dec.) | (46.33<br>46.13 | 4.56<br>4.34 | 11.74)<br>11.53 |
| 3-Chlorophenyl | Cl | Cl | $C_{22}H_{24}ON_5Cl_3 \cdot 2HCl \cdot H_2O$ | 305 (dec.) | (46.22<br>46.20 | 4.94<br>4.64 | 12.25)<br>12.19 |
| Phenyl | $CH_3$ | $CH_3$ | $C_{24}H_{31}ON_5$ | 170–172 | (71.09<br>71.03 | 7.71<br>7.63 | 17.26)<br>17.23 |
| 4-Chlorophenyl | $CH_3$ | $CH_3$ | $C_{24}H_{30}ON_5Cl$ | 199–200.5 | (65.52<br>65.21 | 6.87<br>7.11 | 15.91)<br>15.42 |
| 3,4-Dichlorophenyl | $CH_3$ | $CH_3$ | $C_{24}H_{29}ON_5Cl_2$ | 179–181 | (60.76<br>60.54 | 6.16<br>5.96 | 14.76)<br>14.56 |
| 4-Trifluoromethylphenyl | $CH_3$ | $CH_3$ | $C_{25}H_{30}ON_5F_3$ | 195–197.5 | (64.72<br>64.43 | 6.52<br>6.92 | 15.09)<br>17.26* |
| 3-Trifluoromethylphenyl | $CH_3$ | $CH_3$ | $C_{25}H_{30}ON_5F_3 \cdot 2HCl \cdot 2H_2O$ | 262–265 | (54.20<br>54.52 | 6.19<br>5.85 | 12.64)<br>12.79 |
| Phenyl | H | $CH_3$ | $C_{23}H_{29}ON_5$ | 141–144 | (70.56<br>70.18 | 7.45<br>7.53 | 17.89)<br>18.67 |
| 3-Methoxyphenyl | H | $CH_3$ | $C_{24}H_{31}O_2N_5 \cdot 3HCl \cdot 2.5 H_2O$ | 243–245 | (50.05<br>50.08 | 6.82<br>6.47 | 12.10)<br>12.38 |
| 4-Methoxyphenyl | H | $CH_3$ | $C_{24}H_{31}O_2N_5 \cdot 2HCl \cdot \frac{1}{2}H_2O$ | 260–261 | (57.20<br>57.10 | 6.80<br>6.57 | 13.90)<br>13.73 |
| 3-Chlorophenyl | H | $CH_3$ | $C_{23}H_{28}ON_5Cl$ | 163–164 | (64.85<br>64.85 | 6.63<br>6.59 | 16.44)<br>16.40 |
| 3-Trifluoromethylphenyl | H | $CH_3$ | $C_{24}H_{28}ON_5F_3$ | 159–161 | (62.67<br>62.47 | 6.14<br>6.22 | 15.22)<br>15.16 |
| 4-Trifluoromethylphenyl | H | $CH_3$ | $C_{24}H_{28}ON_5F_3$ | 199–200 | (62.67<br>62.67 | 6.14<br>6.15 | 15.22)<br>15.08 |
| 3,4-Dichlorophenyl | H | $CH_3$ | $C_{23}H_{27}ON_5Cl_2$ | 166–168 | (60.06<br>59.85 | 5.92<br>5.93 | 15.22)<br>15.02 |
| 3-Methoxyphenyl | $CH_3$ | H | $C_{24}H_{31}N_5O_2$ | 91–97 | (68.38<br>68.37 | 7.41<br>7.47 | 16.62)<br>16.38 |
| 4-Chlorostyryl | $CH_3$ | H | $C_{25}H_{29}ON_5Cl \cdot \frac{1}{2}H_2O$ | 111–115 | (65.13<br>65.51 | 6.78<br>6.65 | 15.19)<br>14.86 |
| 4-Chlorophenyl | $CH_3$ | H | $C_{25}H_{28}ON_5Cl$ | 153–155 | (64.85<br>64.72 | 6.62<br>6.66 | 16.44)<br>16.68 |
| 3-Chlorophenyl | $CH_3$ | H | $C_{23}H_{28}ON_4Cl$ | 117–121 | (64.85<br>65.01 | 6.62<br>6.66 | 16.44)<br>16.60 |
| 4-Trifluoromethylphenyl | $CH_3$ | H | $C_{24}H_{28}ON_5F_3$ | 187–189 | (62.73<br>62.82 | 6.14<br>6.28 | 15.24)<br>15.94 |
| 3-Trifluoromethylphenyl | $CH_3$ | H | $C_{24}H_{28}ON_5F_3$ | 127–129 | (62.73<br>62.53 | 6.14<br>6.14 | 15.24)<br>15.16 |
| 4-Trifluoromethylphenyl | Cl | H | $C_{23}H_{25}ON_5ClF_3$ | 190.5–191.5 | (57.56<br>57.43 | 5.25<br>5.13 | 14.59)<br>14.58 |
| 3-Trifluoromethylphenyl | Cl | H | $C_{23}H_{25}ON_5ClF_3$ | 153–155 | (57.56<br>57.22 | 5.25<br>5.13 | 14.59)<br>14.98 |
| 4-Chlorophenyl | Cl | H | $C_{22}H_{25}ON_5Cl_2$ | 123–124 | (59.20<br>58.92 | 5.65<br>5.53 | 15.69)<br>15.52 |
| 3-Chlorophenyl | Cl | H | $C_{22}H_{25}ON_5Cl_2$ | 125–127 | (59.20<br>58.99 | 5.65<br>5.54 | 15.69)<br>15.73 |
| 4-Methoxyphenyl | Cl | H | $C_{23}H_{28}O_2N_5Cl$ | 145–147 | (62.51<br>62.60 | 6.39<br>6.39 | 15.85)<br>15.65 |
| 3-Methoxyphenyl | Cl | H | $C_{23}H_{28}O_2N_5Cl$ | 110–112 | (62.51<br>62.28 | 6.39<br>6.40 | 15.85)<br>15.46 |
| 4-Chlorostyryl | Cl | H | $C_{27}H_{27}ON_5Cl_2$ | 168–170 | (61.02<br>61.00 | 5.76<br>5.60 | 14.82)<br>14.61 |
| Phenyl | Cl | H | $C_{22}H_{26}ON_5Cl$ | 163–166 | (64.15<br>64.00 | 6.36<br>6.26 | 17.00)<br>17.06 |
| 3-Trifluoromethylphenyl | $CF_3$ | H | $C_{24}H_{25}ON_5F_6 \cdot \frac{1}{2}H_2O$ | 140–143 | (55.17<br>55.42 | 5.02<br>4.94 | 13.41)<br>13.89 |
| 4-Trifluoromethylphenyl | $CF_3$ | H | $C_{24}H_{25}ON_5F_6$ | 168–170 | (56.13<br>56.10 | 4.91<br>4.90 | 13.64)<br>13.50 |
| 3-Chlorophenyl | $CF_3$ | H | $C_{23}H_{25}ON_5ClF_3 \cdot \frac{1}{2}H_2O$ | 147–150 | (56.50<br>56.81 | 5.36<br>5.32 | 14.32)<br>14.26 |
| Phenyl | $CF_3$ | H | $C_{23}H_{26}ON_5F_3$ | 171–173 | (62.00<br>62.07 | 5.88<br>5.83 | 15.72)<br>15.49 |
| 4-Chlorophenyl | $CF_3$ | H | $C_{23}H_{25}ON_5ClF_3$ | 173–175 | (57.56<br>57.24 | 5.23<br>5.25 | 14.59)<br>14.49 |
| 3-Methoxyphenyl | $CF_3$ | H | $C_{24}H_{28}O_2N_5F_3$ | 133–149 | (60.62<br>60.16 | 5.93<br>5.85 | 14.73)<br>14.79 |
| 4-Chlorostyryl | $CF_3$ | H | $C_{25}H_{27}ON_5ClF_3$ | 154–180 | (58.30<br>58.74 | 5.48<br>5.27 | 13.60)<br>13.08 |
| 4-Chlorophenyl | $-SO_2N(CH_3)_2$ | H | $C_{24}H_{31}O_3N_6SCl \cdot 2HCl \cdot 2H_2O$ | 260–262 | (45.90<br>46.04 | 5.62<br>5.28 | 13.38)<br>13.57 |
| 3-Trifluoromethylphenyl | $-SO_2N(CH_3)_2$ | H | $C_{25}H_{31}O_3N_6SF_3 \cdot 2HCl \cdot \frac{1}{2}H_2O$ | 175–177 | (47.05<br>47.07 | 5.10<br>5.21 | 13.01)<br>13.19 |
| 4-Trifluoromethylphenyl | $-SO_2N(CH_3)_2$ | H | $C_{25}H_{31}O_3N_6SF_3 \cdot HCl \cdot 1.3H_2O$ | 246–247 | (50.45<br>50.36 | 5.53<br>5.35 | 14.12)<br>14.08 |
| 3,4-Dichlorophenyl | $-SO_2N(CH_3)_2$ | H | $C_{24}H_{30}O_3N_6SCl_2 \cdot 1\frac{1}{2}H_2O$ | 191–195 | (49.87<br>49.86 | 5.58<br>5.14 | 14.54)<br>14.53 |
| Phenyl | $-SO_2N(CH_3)_2$ | H | $C_{24}H_{32}O_3N_6S \cdot 2HCl \cdot H_2O$ | 273–276 | (49.96<br>50.29 | 6.29<br>5.78 | 14.57)<br>14.28 |
| 3-Methoxyphenyl | $-SO_2N(CH_3)_2$ | H | $C_{25}H_{34}O_4N_6S \cdot 2HCl \cdot 1\frac{1}{2}H_2O$ | 268–270 | (49.15<br>48.94 | 6.27<br>5.88 | 13.75)<br>13.78 |
| 4-Methoxyphenyl | $-SO_2N(CH_3)_2$ | H | $C_{25}H_{34}O_4N_6S \cdot 2HCl \cdot \frac{1}{2}$ | 270–273 | (50.55 | 5.77 | 14.15) |

-continued

| R | $R_1$ | $R_2$ | Empirical Formula | m.p., °C. | Elemental Analysis,% (Theoretical % in brackets) | | |
|---|---|---|---|---|---|---|---|
| | | | | | C | H | N |
| 3-Chlorophenyl | $-SO_2N(CH_3)_2$ | H | $C_{24}H_{31}O_3N_6SCl \cdot 2HCl \cdot H_2O$ | 280–282 | 50.66 (47.25 | 6.08 5.78 | 14.30 13.78) |
| Phenyl | $OCH_3$ | H | $C_{23}H_{29}O_2N_5$ | 145–147.5 | 47.02 (67.79 | 5.44 7.17 | 14.04 17.19) |
| 3-Chlorophenyl | $OCH_3$ | H | $C_{23}H_{28}O_2N_5Cl$ | 96–99 | 67.80 (62.51 | 7.11 6.39 | 17.18 15.85) |
| 3-Methoxyphenyl | $OCH_3$ | H | $C_{24}H_{31}O_3N_5$ | 93–96 | 62.49 (65.88 | 6.33 7.13 | 15.83 16.01) |
| 4-Trifluoromethyl-phenyl | $OCH_3$ | H | $C_{24}H_{28}O_2N_5F_3$ | 145–149 | 65.59 (60.62 | 7.07 5.93 | 15.95 14.73) |
| 3-Trifluoromethyl-phenyl | $OCH_3$ | H | $C_{24}H_{28}O_2N_5F_3$ | 121–123 | 60.37 (60.62 | 5.83 5.93 | 14.80 14.73) |
| 4-Chlorostyryl | $OCH_3$ | H | $C_{25}H_{30}O_2N_5Cl$ | 115–118 | 60.20 (64.16 | 5.87 6.46 | 14.51 14.96) |
| 3,4-Dichlorophenyl | $OCH_3$ | H | $C_{23}H_{27}O_2N_5Cl_2$ | 113–115 | 63.51 (57.99 57.64 | 6.56 5.71 5.62 | 14.61 14.70 14.78 |

*structure validated by mass spectral analysis.

EXAMPLE 8

1-[3-(1-Piperidinyl)propyl]-2-(4-trifluoromethylbenzamido)benzimidazole

The reaction of o-chloronitrobenzene (248 g., 1.0 mole) with 1-(3-aminopropyl)piperidine (2.3 g., 1.5 mole) was carried out as described in Example I for 1-(3-aminopropyl)-4-methylpiperazine. In this instance the product isolated was 2-[3-(1-piperidinyl)-propylamino]nitrobenzene. An analytical sample was obtained by dissolving a portion of the product in isopropyl alcohol, treatment with dry hydrogen and crystallization from isopropanol-ether, to afford colorless crystals, m.p. 177°–178° C.

Anal. Calc'd for $C_{14}H_{22}O_2N_3 \cdot HCl \cdot H_2O$: C, 52.74; H, 7.90; N, 13.17. Found: C, 52.90; H, 7.70; N, 13.96.

The balance of the 2-[3-(1-piperidinyl)propylamino]-nitrobenzene was reduced to the corresponding N-substituted o-phenylenediamine by means of stannous chloride in concentrated hydrochloric acid as described in Example 1 for the corresponding 4-methylpiperazino compound. The product, N-[3-(1-piperidinyl)propyl]-o-phenylenediamine, was isolated as the hydrochloride salt by crystallization from isopropanol, m.p. 208°–210° C.

Anal. Calc'd for $C_{14}H_{23}N_3 \cdot 2HCl$: C, 54.93; H, 8.23; N, 13.73. Found: C, 54.37; H, 8.11; N, 13.61.

To a stirred suspension of 20.0 g. (0.086 mole) of N-[3-(1-piperidinyl)propyl]-o-phenylenediamine in 80 ml. water, 20 ml. of isopropanol was added to obtain a homogenous solution. With continued stirring, 21.2 g. (0.200 mole) of cyanogen bromide was added in portions over a one hour period. Room temperature was maintained throughout the addition. After stirring for an additional 2 hours the reaction mixture was allowed to stand overnight. The mixture was then poured into ice-water, made strongly alkaline with KOH and extracted with methylene chloride. The extracts were evaporated to a red oil which crystallized from ether, 7.9 g. (36% yield), m.p. 176°–178° C. An analytical sample of 1-[3-(1-piperidinyl)propyl]-2-amino benzimidazole was obtained by crystallization from benzene-cyclohexane, m.p. 179°–181° C.

Anal. Calc'd for $C_{15}H_{22}N_4$: C, 69.73; H, 8.58; N, 21.69. Found: C, 69.69; H, 8.72; N, 21.83.

Two grams (7.75 millimoles) of the above prepared 1-substituted 2-aminobenzimidazole was dissolved in 15 ml. of hexamethylphosphoric triamide and the solution cooled to 5° C. To the stirred solution 1.62 g. (7.75 millimoles) of 4-trifluoromethylbenzoyl chloride was added dropwise while maintaining the reaction temperature below 10° C. The mixture was allowed to warm to room temperature, then poured into 200 ml. water and adjusted to pH 10 with solid $Na_2CO_3$. The alkaline solution was extracted with 2 × 75 ml. of benzene. The benzene extracts were washed with saturated aqueous NaCl solution and the organic layer dried over $MgSO_4$. After filtering, the solvent was removed in vauco to afford a waxy solid. This was slurried with pentane to give a white flocculent solid, 2.03 g. (61% crude yield) which upon crystallization from a mixture of isopropyl ether and acetone gave pure 1-[3-(1-piperidinyl)propyl]-2-(4-trifluoromethylbenzamido)benzimidazole hemihydrate, m.p. 182°–184° C.

Anal. Calc'd for $C_{23}H_{25}ON_4F_3 \cdot \frac{1}{2}H_2O$: C, 62.18; H, 5.46; N, 12.74. Found: C, 61.93; H, 5.65; N, 12.48.

EXAMPLE 9

Following the procedure of Example 8, but making suitable substitutions for benzoyl chloride in the acylation step, the following 2-aminobenzimidazoles of the general structure II were prepared.

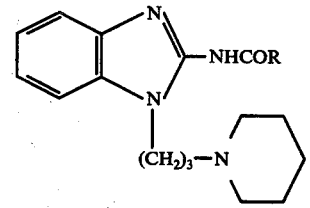

II

| R | m.p., °C. | Empirical Formula | Elemental Analysis, % (Theoretical % in brackets) | | |
|---|---|---|---|---|---|
| | | | C | H | N |
| 3-Fluorophenyl | 236–237 | $C_{22}H_{25}ON_4F \cdot HCl \cdot H_2O$ | (60.75 60.93 | 6.49 6.29 | 12.87) 12.70 |
| 3-Trifluoromethylphenyl | 244–246 | $C_{23}H_{25}ON_4F_3 \cdot HCl \cdot 1/2H_2O$ | (58.04 58.25 | 5.71 5.60 | 11.76) 11.82 |
| Styryl | 98–100 | $C_{24}H_{28}ON_4$ | (74.20 74.05 | 7.26 7.26 | 14.41) 14.36 |
| 2-Furyl | 252–254 | $C_{20}H_{24}O_2N_4 \cdot 2HCl \cdot 1/2H_2O$ | (55.31 55.40 | 6.27 6.17 | 12.89) 13.06 |
| 3-Chlorophenyl | 255–257 | $C_{22}H_{25}ON_4Cl \cdot HCl \cdot 1/3H_2O$ | (60.40 60.39 | 6.04 6.01 | 12.75) 12.68 |
| 3-Methoxyphenyl | 92–95 | $C_{23}H_{28}O_2N_4 \cdot 1/3H_2O$ | (69.38 69.26 | 7.17 7.03 | 14.06) 14.00 |
| 3,4-Dichlorophenyl | 279–281 | $C_{22}H_{24}ON_4Cl_2 \cdot HCl$ | (56.48 56.35 | 5.34 5.39 | 11.98) 12.07 |
| 4-Chloro | 167–169 | $C_{22}H_{25}ON_4Cl \cdot$ | (57.39 | 6.35 | 12.16) |

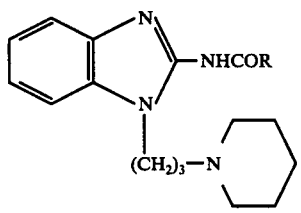

II

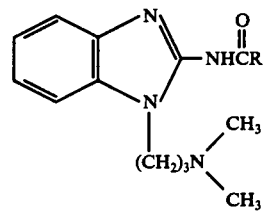

III

| R | m.p., °C. | Empirical Formula | Elemental Analysis, % (Theoretical % in brackets) | | |
|---|---|---|---|---|---|
| | | | C | H | N |
| | | HCl . 1 . 5H₂O | 56.95 | 6.56 | 12.55 |

EXAMPLE 10

1-[3-(Dimethylamino)propyl]-2-(4-Chlorobenzamido)-benzimidazole

Employing the procedure described in the previous examples, 1-[3-(dimethylamino)propyl]-2-aminobenzimidazole, m.p. 145°–146° C., was prepared from o-chloronitrobenzene and N,N-dimethyltrimethylenediamine via catalytic reduction of the nitro group of the intermediate 2-[3-(dimethylamino)propylamino]nitrobenzene and cyclization with cyanogen bromide in an isopropanol water medium.

1-[3-(dimethylamino)propyl]-2-aminobenzimidazole (3.0 g., 13.7 millimoles) and 5.7 g. $K_2CO_3$ (anhydrous) were suspended in 40 ml. methylene chloride and the mixture cooled to 0° C. under a nitrogen atmosphere. p-Chlorobenzoyl chloride (2.89 g., 16.5 millimoles) dissolved in 10 ml. of $CH_2Cl_2$ was added dropwise over a 10 minute period. The resulting mixture was stirred at 0° C. for an additional 30 minutes, then allowed to come to room temperature and allowed to stir overnight. The reaction mixture was poured into a mixture of 250 ml. water and 200 ml. $CH_2Cl_2$. After shaking and separation of layers, the aqueous phase was washed with an additional 50 ml. of $CH_2Cl_2$. The combined organic layers were dried over $Na_2SO_4$, then concentrated to a residual oil. Dry methanol, 100 ml. was used to dissolve the residue and the solution was saturated with dry hydrogen chloride. The resulting yellow solution was concentrated to dryness and 50 ml. of methanol added to dissolve the residue. After addition of 200 ml. of ethyl acetate a solid precipitate formed; this was collected by filtration and dried. After recrystallization from methanol-ethyl ether, a colorless solid, 1-[3-(dimethylamino)propyl]-2-(4-chlorobenzamido)benzimidazole dihydrochloride monohydrate, 2.74 g. (45% yield) was obtained, m.p. 227°–229° C.

Anal. Calc'd for $C_{19}H_{21}ON_4Cl.2HCl.H_2O$: C, 50.96; H, 5.63; N, 12.51. Found: C, 50.51; H, 5.42; N, 12.69.

EXAMPLE 11

Employing the above procedures the following 2-amido benzimidazoles of the general structure III were prepared.

| R | m.p., °C. | Empirical Formula | Elemental Analysis,% (Theoretical % in brackets) | | |
|---|---|---|---|---|---|
| | | | C | H | N |
| 3-Trifluoro-methylphenyl | 225–228 | $C_{20}H_{21}ON_4F_3$ . 2HCl . H₂O | (49.90) 50.05 | 5.24 4.99 | 11.64) 11.97 |
| -CH₂OCH₃ | 221–224 | $C_{15}H_{22}O_2N_4$ . 2HCl . 2H₂O | (47.24) 46.73 | 6.87 6.85 | 14.69) 14.58 |
| 4-Methoxy-phenyl | 239–243 (dec.) | $C_{20}H_{24}O_2N_4$ . 2HCl . 3/4H₂O | (54.73) 54.81 | 6.32 6.66 | 12.77) 12.81 |
| 2-Chloro phenyl | 197–201 | $C_{19}H_{21}ON_4Cl$ . 2HCl . 2 . 5H₂O | (48.06) 48.04 | 5.94 5.44 | 11.80) 12.15 |
| 3-Methyl-phenyl | 160–165 | $C_{20}H_{24}ON_4$ . 2HCl . 2 . 5H₂O | (52.86) 53.25 | 6.88 6.19 | 12.33) 12.63 |
| 2-Chloro-styryl | 258–261 (dec.) | $C_{21}H_{23}ON_4Cl$ . 2HCl | (55.34) 54.74 | 5.53 6.05 | 12.29) 12.56 |
| 3-Methoxy-phenyl | 162–168 (dec.) | $C_{20}H_{24}O_2N_4$ . 2HCl . 2 . 5H₂O | (51.06) 51.29 | 6.64 6.04 | 11.91) 11.94 |
| 4-Chloro-styryl | 153–154 | $C_{21}H_{23}ON_4Cl$ | (65.88) 65.50 | 6.04 6.04 | 14.63) 14.55 |
| Phenyl | 188–193 | $C_{19}H_{22}ON_4$ . 2HCl . 1 . 5H₂O | (54.03) 54.58 | 6.44 6.04 | 13.27) 13.43 |
| 3-Chloro-phenyl | 158–160 | $C_{19}H_{21}ON_4Cl$ | (63.95) 63.83 | 5.93 5.75 | 15.70) 15.76 |
| 3,4-Dichloro-phenyl | 187–188 | $C_{19}H_{20}ON_4Cl_2$ | (58.32) 58.17 | 5.15 5.13 | 14.32) 14.18 |

EXAMPLE 12

1-[2-(N-Morpholino)propyl]-2-(3-chlorobenzamido)-benzimidazole

Following the procedure of Example 1 but using N-(3-aminopropyl)morpholine in place of 1-(3-aminopropyl)-4-methyl piperazine, afforded a good yield of N-[3-(N-morpholino)propyl]-o-phenylenediamine, isolated as an oil.

Ethyl alcohol (15 ml.) was added to N-[3-(N-morpholino)propyl]-o-phenylenediamine (18.8 g., 0.080 mole) suspended in 80 ml. of water. Cyanogen bromide (19.0 gm. 0.18 mole) was then added to small portions over a period of 4 hrs. This produced an exothermic reaction which caused the temperature to rise to 52° C. After allowing the reaction mixture to cool to 25° C. it was then poured over ice water and basified with 10N KOH, extracted with 4 × 100 ml. portions of chloroform, dried over magnesium sulfate and evaporated to dryness yielding 9.2 g. of 1-[3-(N-morpholino)propyl]-2-aminobenzimidazole, m.p. 195°–199° C.

A 1 gm. sample of the above was recrystallized from 20 ml. of hot isopropyl alcohol, filtered hot and allowed to precipitate overnight yielding 0.831 gm., m.p. 201°–203° C.

Anal. Calc'd for $C_{14}H_{20}N_4O$: C, 64.59; H, 7.44; N, 21.52. Found: C, 64.35; H, 7.96; N, 21.65.

1-[3-(N-morpholino)propyl]-2-aminobenzimidazole, 2.60 g. (0.010 mole) was suspended in 25 ml. of methylene dichloride. Potassium carbonate (4.15 g., 0.030 mole) was added and the mixture cooled to about 10° C. in an ice bath. m-Chlorobenzoyl chloride (1.92 gm. 0.011 mole) in 5 ml. of methylene dichloride was added dropwise to the mixture. The mixture was then poured into ice water, extracted with methylene dichloride and the extracts stirred with ether to precipitate traces of unreacted starting material which was then removed by filtration. The mother liquor was evaporated to dryness, the resultant solid dissolved in hot cyclohexane, filtered hot and then allowed to cool slowly. A reddish oil precipitated which was then dissolved in methylene dichloride, treated with activated charcoal and filtered. The filtrate was then evaporated to give 3.8 g. of yellow oil which was then slurried in ethyl ether to yield 0.967 g. of white crystals, m.p. 164°-166° C. The mother liquor was evaporated to dryness, dissolved in 30 ml. of hot isopropyl alcohol and filtered hot; crystals formed slowly. These crystals were filtered and dried yielding 1.374 g. of 1-[3-(N-morpholino)propyl]-2-(3-chlorobenzamido)benzimidazole, m.p. 165°-166° C.

Anal. Calc'd for $C_{21}H_{23}N_4O_2Cl$: C, 63.23; H, 5.81; N, 14.05. Found: C, 62.94; H, 5.86; N, 13.85.

EXAMPLE 13

Employing the above procedure, with substitution of the appropriate acid chloride for m-chlorobenzoyl chloride in each case, gave the following compounds of the general structure IV.

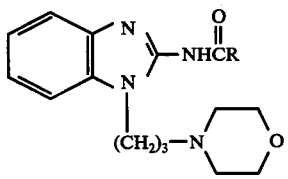

IV

| R | m.p., °C. | Empirical Formula | Elemental Analysis,% (Theoretical % in brackets) | | |
|---|---|---|---|---|---|
| | | | C | H | N |
| 4-Chloro-phenyl | 163–171 (dec.) | $C_{21}H_{23}O_2N_4Cl \cdot \frac{1}{2}H_2O$ | (61.83) 62.38 | 5.93 5.90 | 13.74 13.78 |
| 3-Methoxy-phenyl | 230–232 (dec.) | $C_{22}H_{26}O_3N_4 \cdot HCl \cdot H_2O$ | (58.85) 58.42 | 6.51 5.80 | 12.48 12.05 |
| 4-Methoxy-phenyl | 144–173 | $C_{22}H_{26}O_3N_4 \cdot \frac{1}{2}H_2O$ | (65.49) 66.06 | 6.75 6.60 | 13.89 13.47 |
| -CH$_2$OCH$_3$ | 115–122 | $C_{17}H_{24}O_3N_4$ | (61.42) 60.95 | 7.28 7.34 | 16.86 16.97 |
| 2-Fluoro-phenyl | 114–145 (dec.) | $C_{21}H_{23}O_2N_4F \cdot 2HCl \cdot 2H_2O$ | (51.32) 51.80 | 5.95 5.51 | 11.40 11.59 |
| 3-Trifluoro-methyl-phenyl | 123–147 (dec.) | $C_{22}H_{23}O_2N_4F_3 \cdot 2HCl \cdot H_2O$ | (50.48) 50.58 | 5.20 5.12 | 10.71 11.12 |
| (CH$_3$)$_3$CC-H$_2$- | 137–142 (dec.) | $C_{20}H_{30}O_2N_4 \cdot 2HCl \cdot H_2O$ | (53.45) 53.38 | 7.62 7.20 | 12.47 12.05 |
| 3-Methyl-phenyl | 112–120 (dec.) | $C_{22}H_{26}O_2N_4 \cdot 2HCl \cdot 2.5H_2O$ | (53.22) 53.38 | 6.29 5.85 | 11.28 11.23 |
| Phenyl | 105–115 (dec.) | $C_{21}H_{24}O_2N_4 \cdot 2HCl \cdot 2H_2O$ | (53.70) 54.09 | 6.38 6.25 | 11.85 11.73 |
| 4-Trifluoro-methyl-phenyl | 168–170 | $C_{22}H_{23}O_2N_4F_3$ | (61.10) 60.95 | 5.36 5.34 | 12.96 13.01 |

EXAMPLE 14

Employing the above described procedures 1-[3-(4-benzyl-1-piperazinyl)propyl]-2-aminobenzimidazole was prepared and recrystallized from methanol, m.p. 220°-222° C.

Anal. Calc'd for $C_{21}H_{27}N_5$: C, 72.17; H, 7.79; N, 20.04. Found: C, 71.97; H, 7.78; N, 19.97.

Upon acylation with the appropriate acid chloride the following amides of the general structure V were prepared.

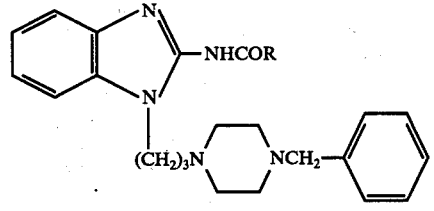

V

| R | m.p., °C. | Empirical Formula | Elemental Analysis,% (Theoretical % in brackets) | | |
|---|---|---|---|---|---|
| | | | C | H | N |
| Phenyl | 145–146.5 | $C_{28}H_{31}ON_5$ | (74.14) 73.87 | 6.89 6.84 | 15.44 15.42 |
| 4-Trifluoro-methyl-phenyl | 165–167 | $C_{29}H_{30}ON_5F_3$ | (66.78) 66.63 | 5.80 5.81 | 13.43 13.34 |
| 3-Trifluoro-methyl-phenyl | 144–145.5 | $C_{29}H_{30}ON_5F_3$ | (66.78) 67.12 | 5.80 5.84 | 13.43 13.53 |
| 4-Methoxy-phenyl | 188–119.5 | $C_{29}H_{33}O_2N_5 \cdot \frac{1}{2}H_2O$ | (70.71) 70.90 | 6.96 6.86 | 14.22 14.12 |
| 3,4-Dichloro-phenyl | 153–155 | $C_{28}H_{29}ON_5Cl_2$ | (64.37) 64.53 | 5.59 5.72 | 13.40 13.41 |

EXAMPLE 15

To a solution composed of 75 ml. ethanol and 1 ml. glacial acetic acid was added 2-(4-trifluoromethylbenzamido)-1-[3-(4-benzyl-1-piperazinyl)propyl]benzimidazole (500 mg., 0.96 millimole) and 100 mg. of 10% Pd/C catalyst. The mixture was shaken on a Paar apparatus at about 2 atm. pressure of hydrogen and 40° C. for 2.5 hrs. at which time the reaction was complete. The catalyst was removed by filtration and the filtrate was evaporated in vacuo to yield a white solid, which on trituration under acetone yielded 300 mg. (63.9% yield) of 2-(4-trifluoromethylbenzamido)-1-[3-(1-piperazinyl)propyl]benzimidazole, as a white crystalline solid, m.p. 184°-185° C.

Anal. Calc'd for $C_{22}H_{24}ON_5F_3 \cdot CH_3COOH$: C, 58.65; H, 5.74; N, 14.25. Found: C, 58.55; H, 5.74; N, 14.05.

EXAMPLE 16

Employing the procedures of Examples 14 and 15 the following amides of the general structure VI were prepared.

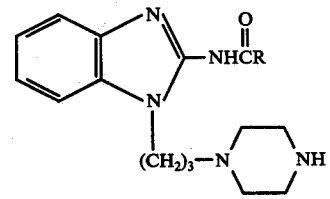

VI

| R | m.p., °C. | Empirical Formula | Elemental Analysis,% (Theoretical % in brackets) | | |
|---|---|---|---|---|---|
| | | | C | H | N |
| Phenyl | 190 (dec.) | $C_{21}H_{25}ON_5 \cdot 3HCl \cdot \frac{1}{2}H_2O$ | (51.86) 51.72 | 6.06 6.16 | 14.39 14.37 |
| 3-Trifluoro-methyl-phenyl | 220 (dec.) | $C_{22}H_{24}ON_5F_3 \cdot 3HCl$ | (48.86) 49.01 | 5.03 4.93 | 12.93 12.95 |

EXAMPLE 17

2-(3-Trifluoromethylbenzamido)-2-[(4-methyl-1-piperazino)propyl]-imidazo[4,5-b]pyridine In a 2 liter, three-necked flask fitted with condenser, dropping funnel, thermometer, magnetic stirrer and nitrogen inlet was placed 71.8 g. (0.456 mole) 1-(3-aminopropyl)-4-methyl piperazine and 150 ml. of ethanol. The solution was heated at reflux and a solution of 65.0 g. 2-chloro-3-nitropyridine dissolved in 500 ml. of warm ethanol was added dropwise over 90 minutes. The dark yellow reaction mixture was maintained at reflux of an additional hour then cooled to ambient temperature. The solvent was then removed in vacuo to obtain a yellow-brown semi-solid residue. The residue was partitioned between 200 ml. each of aqueous 1N HCl and methylene chloride, and aqueous phase washed with 100 ml. $CH_2Cl_2$. The aqueous portion was made basic with 6N NaOH and extracted with 3 × 250 ml. $CH_2Cl_2$. The combined organic layers were dried over $Na_2SO_4$ and the solvent evaporated to afford 2-[3-(4-methyl-1-piperazinyl)propylamino]-3-nitropyridine as a red-yellow oil which crystallized on standing at room temperature; yield 82.9 g. (72%).

The product of the above reaction, 82.8 g. (0.269 mole) was dissolved in 250 ml. of 6N hydrochloric acid and reacted with a solution of 234 g. (1.04 mole) stannous chloride hydrate in 250 ml. of 6N HCl as described in Example 1. The aqueous reaction mixture was adjusted to pH 7 with solid $Na_2CO_3$ while cooling in an ice-bath, then treated with $NH_4OH$ to bring to pH 10. The pale yellow precipitate was collected by filtration and washed with methanol (1 liter). The dry filter cake was partitioned between 50% aqueous potassium hydroxide and benzene. The aqueous layer was extracted twice more with benzene then extracted with ethyl acetate (5 × 800 ml.) The combined organic layers were concentrated in vacuo to obtain 71.6 g. (97% yield) of 2-[3-(4-methyl-1-piperazinyl)propylamino]-3-aminopyridine.

A portion of the above product, 61.6 g. (0.247 mole), in 1000 ml. of water was treated with 58 g. (0.545 mole) cyanogen bromide in 500 ml. of water at 30°-35° C. over 1 hour. The reaction mixture was then stirred at 50° C. for 2.5 hrs. and allowed to cool to room temperature overnight. The reaction mixture was poured onto 400 ml. of cold 50% KOH and the basic solution was extracted with ethyl acetate (4 liters) until the extracts became colorless. The combined organic layers were dried over $MgSO_4$ and the solvent removed at reduced pressure to obtain 53.1 g. of 2-amino-3-[3-(4-methyl-1-piperazino)propyl]imidazo[4,5-b]pyridine as a brown solid. Tan crystals, 31 g. (45% yield), m.p. 176°-177° C. were obtained upon slurrying with acetone.

Anal Calc'd for $C_{14}H_{22}N_6 \cdot \frac{1}{2}H_2O$: C, 59.96; H, 8.15; N, 29.98. Found: C, 60.07; H, 7.83; N, 29.72.

A portion of the above imidazo[4,5-b]pyridine derivative, 4.1 g. (0.015 mole) was dissolved in 10 ml. of hexamethylphosphoric triamide (HMPT). To this solution was added over a 15 minute period a solution of 3.12 g. (0.015 mole) 3-trifluoromethyl benzoyl chloride in 10 ml. HMPT while maintaining the reaction mixture below 10° C. The resulting mixture was stirred for 1.5 hours, then poured into 100 ml. of water. After adjusting to pH 10 with 10% NaOH a pale yellow precipitate formed. This was extracted with benzene (100 ml.) dried over $MgSO_4$, filtered and the solvent removed in vacuo to obtain 3.5 g. of white solid. This was recrystallized from 100 ml. of 1:1 benzene-hexane to obtain 2-(3-trifluoromethylbenzamido)-3-[3-(4-methyl-1-piperazino)propyl]imidazo[4,5-b]pyridine as a colorless solid, 3.2 g. (48% yield), m.p. 157°-159° C. The mass spectrum showed a molecular ion at M/e 446 and was in agreement with the designated structure.

Anal. Calc'd for $C_{22}H_{25}ON_6F_3 \cdot 1.5H_2O$: C, 56.71; H, 5.45; N, 18.03. Found: C, 56.99; H, 5.45; N, 17.82.

EXAMPLE 18

By substitution of the appropriate acid chlorides in the procedure of Example 16, 2-amino-3-[3-(4-methyl-1-piperazino)propyl]imidazo[4,5-b]pyridine was converted to other 2-amido compounds of the general structure VII.

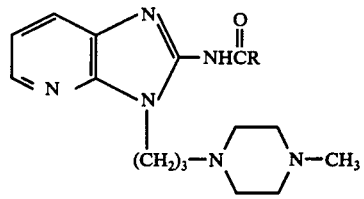

VII

| R | m.p.,° C. | Empirical Formula | Elemental Analysis,% (Theoretical % in brackets) | | |
|---|---|---|---|---|---|
| | | | C | H | N |
| 4-Trifluoromethylphenyl | 272-275 | $C_{22}H_{25}ON_6F_3 \cdot$ 2HCl . $H_2O$ | (49.16 49.05 | 5.43 5.04 | 15.63) 15.24 |
| 3,4-Dichlorophenyl | 282-284 | $C_{21}H_{24}ON_6Cl_2 \cdot$ 3HCl | (45.30 45.70 | 4.89 4.88 | 15.10) 14.97 |
| 3-Chlorophenyl | 188-189 | $C_{21}H_{25}ON_6Cl$ | (61.08 60.48 | 6.10 6.01 | 20.36) 20.03 |
| Phenyl | 261-262 | $C_{21}H_{26}ON_6 \cdot$ 3HCl | (51.70 51.54 | 5.99 6.12 | 17.23) 17.38 |
| 4-Methoxyphenyl | 261-262 | $C_{22}H_{28}O_2N_6 \cdot$ 3HCl . $\frac{1}{2}H_2O$ | (50.14 49.85 | 6.12 5.99 | 15.95) 15.95 |
| 3-Methoxyphenyl | 273-275 | $C_{22}H_{28}O_2N_6 \cdot$ 2HCl . $\frac{3}{4}H_2O$ | (53.54 53.48 | 6.39 6.04 | 17.03) 17.03 |

EXAMPLE 19

To a solution of 19.5 g. (0.070 mole) 2-[3-(4-methyl-1-piperazinyl)propylamino]nitrobenzene in 250 ml. of ethanol was added 1.0 g. of 10% Palladium on carbon catalyst. The mixture was shaken on a Paar apparatus at about 2 atm. pressure of hydrogen at room temperature for 90 minutes. The hydrogen uptake was quantitative. The catalyst was removed by filtration and the solvent evaporated in vacuo to afford a dark red oil which was purified by distillation (b.p. 160°-168°/0.02 mm) to give 15.3 g. (88% yield) on an oil which crystallized upon standing at room temperature. It gave one spot on thin-layer chromatography and was identified as N-[3-(4-methyl-1-piperazinyl)propyl]-o-phenylenediamine by comparison with an authentic sample.

To a cooled solution (18° C.) of N-[3-(4-methyl-1-piperazinyl)propyl]o-phenylenediamine (2.48 g., 0.01 mole) in benzene (50 ml.) was added benzoyl imidocarbonyl chloride (2.02 g., 0.01 mole) dissolved in benzene (15 ml.) at a rate sufficient to keep the temperature below 20° C. After stirring overnight at room temperature, the reaction mixture was treated with 1N NaOH (40 ml.) and $H_2O$ (10 ml.) and then extracted with $CHCl_3$ (3 × 70 ml.). The organic layers were combined, dried ($MgSO_4$), evaporated in vacuo to give 3 g. of a red oil. The crystals which were obtained on treatment of the oil with ethyl acetate were filtered and washed (petroleum ether/ethyl acetate 2/1) yielding 1.2 g. of 1-[3-(4-methyl-1-piperazinyl)propyl]-2-benzamido-benzimidazole, m.p. 142°–143° C. Evaporation of the mother liquors and treatment as above yielded an additional 700 mg. of product, m.p. 142°–143° C. Recrystallization of the combined solids yielded 1 g. (yield 26.5%), m.p. 146°–147° C.

The same compound was obtained as follows by an alternate route:

To a solution of N-[3-(4-methyl-1-piperazinyl)propyl]-o-phenylenediamine (1.24 g., 0.005 mole) in ethanol (50 ml.) was added 0.82 g. (0.005 mole) benzoyl isothiocyanate in one portion. After stirring overnight at room temperature, the solution was evaporated in vacuo to a red oil, which was chromatographed on a silica gel column yielding on crystallization from ethyl acetate 390 mg. of 1-[3-(4-methyl-1-piperazinyl)propyl]-2-benzamido-benzimidazole (yield 20.6%), m.p. 147°–148° C. The material isolated by this synthesis was identical in all respects to an authentic sample.

EXAMPLE 20

To a suspension of S-methylisothiourea hemisulfate (21 g., 0.15 mole) in $H_2O$ (90 ml.) at 10° C. (ice-water bath) was added NaOH pellets (6 g., 0.15 mole) dissolved in $H_2O$ (30 ml.). Then 3,4-dichlorobenzoyl chloride (63 g., 0.30 mole) and sodium carbonate (18.6 g., 0.15 mole) dissolved in $H_2O$ (150 ml.), each of which were divided into five equal portions, were added in alternate portions. The resultant white precipitate was stirred at room temperature for 2 hours. Following filtration of the precipitate, the solids were washed with $H_2O$ (200 ml.), and Pet. ether (100 ml.) and triturated under warm dimethylformamide to yield 46 g. of S-methyl-1,3-(3,4-dichlorobenzoyl)-isothiourea (yield 70%) m.p. 228°–230° C. A small sample on recrystallization from dimethylformamide gave an analytical sample, m.p. 232°–234° C.

Anal. Calc'd for $C_{16}H_{10}O_2N_2Cl_4S$: C, 44.06; H, 2.31; N, 6.42. Found: C, 44.02; H, 2.47; N, 6.44.

A white suspension of o-phenylenediamine (1.08 g., 0.01 mole) and S-methyl- 1,3-(3,4-dichlorobenzoyl)-isothiourea (4.36 g., 0.01 mole) in dimethylformamide was heated to reflux at about 155° C. All material went into solution and evolution of methyl mercaptan was observed. After 2 hrs. at reflux, the reaction was cooled and diluted with $H_2O$ (140 ml.). The resultant yellow solid was filtered and washed with cold isopropyl alcohol to yield 2.54 g. yield 83%) of 2-(3,4-dichlorobenzamido)-benzimidazole, m.p. 251°–252.5° C. A small sample on recrystallization from isopropanol/water gave an analytical sample, m.p. 250.5°–252° C.

Anal. Calc'd for $C_{14}H_9ON_3Cl_2$: C, 54.93; H, 2.96; N, 13.73. Found: C, 54.75; H, 3.08; N, 13.58.

To a solution of 2-(3,4-dichlorobenzamido)-benzimidazole (2.0 g., 0.0065 mole) in dimethylformamide (100 ml.) was added NaH (940 mg., 0.0195 mole) at a rate sufficient to maintain the temperature below 40° C. After evolution of $H_2$ subsided, 4-methyl-1-piperazinyl propyl bromide dihydrobromide (2.5 g., 0.0065 mole), obtained by the above-mentioned method of Kriesel and Gisvold, was added in three portions (waiting for cessation of $H_2$ evolution). After 1 hour, additional NaH (470 mg., 0.00975 mole) and 4-methyl-1-piperazinyl propyl bromide.2HBr (1.25 g., 0.00327 mole) was added and the reaction mixture was stirred overnight at room temperature. The reaction was halted by the addition of $H_2O$ (100 ml.). The reaction mixture was extracted with $CHCl_3$ and the organic layers were combined, dried ($MgSO_4$) and evaporated in vacuo to give an oil. The crystalline solid which formed on standing gave, after treatment with hexane/ethyl acetate (2:1), 1.2 g. (41% yield) of pure 1-[3-(4-methyl-1-piperazinyl)propyl]-2-(3,4-dichlorobenzamido)-benzimidazole m.p. 166°–167.5° C. An additional 900 mg. of product containing a trace of starting material was isolated from the mother liquors and absorbed onto SilicAR (CC-7, 20 g.). The SilicAR was washed sequentially with benzene, ethyl acetate and methanol (300 ml.). Concentration of the combined ethyl acetate/methanol washes gave an additional 550 mg. (Overall yield 62%) of pure solid, m.p. 163.5°–165° C. This material was identical to an authentic sample on comparison by thin-layer chromatography, melting point and mixed melting point.

EXAMPLE 21

N-[3-(4-Methyl-1-piperazinyl)propyl]-o-phenylenediamine (2.48 g., 0.01 mole), prepared as described in Example 1, and S-methyl-1,3-(3,4-dichlorobenzoyl)-isothiourea, as prepared in the preceding Example, (4.36 g. 0.01 mole) were combined and fused (Oil bath temp. 135°–140° C.). The melt was held at this temperature until all evolution of methyl mercaptan subsided (2 hrs.). The reaction mixture was then treated with ethanol (25 ml.) and refluxed for an additional 1 hour. The off-white crystals that formed on cooling were filtered and recrystallized from boiling acetone to yield 2.15 g. of 1-[3-(4-methyl-1-piperazinyl)-propyl]-2-(3,4-dichlorobenzamido)-benzimidazole (yield 48%), m.p. 166°–167.5° C. Concentration of the mother liquor to about ¼ volume afforded an additional 400 mg., m.p. 163°–164° C. (overall yield 57%). The melting point, nuclear magnetic resonance spectrum and mass spectrum were identical to those of an authentic sample.

EXAMPLE 22

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient 1-[3-(4-methyl-1-piperazinyl)propyl]2-(3,4-dichlorobenzamido)benzimidazole dimesylate to provide tablets containing 100 and 250 mg. of active ingredient per tablet. The compositions are each compressed into tablets, each weighing 360 mg., by conventional means.

EXAMPLE 23

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |

| -continued | |
|---|---|
| Magnesium stearate B | 0.35 |

To this blend is added sufficient 1-[3-(4-methyl-1-piperazinyl)propyl]-2-(3,4-dichlorobenzamido)benzimidazole dimesylate to provide capsules containing 50, 100 and 250 mg. of active ingredient per capsule. The compositions are filled into conventional hard gelatin capsules in the amount of 350 mg. per capsule.

EXAMPLE 24

Injectable Preparation

One thousand grams of 1-[3-(4-methyl-1-piperazinyl)propyl]-2-(3,4-dichlorobenzamido)benzimidazole dimesylate and 2500 grams of sodium ascorbate are intimately mixed and ground. The ground mixture is placed in vials and sterilized with ethylene oxide after which the vials are sterilely stoppered. For intravenous administration, sufficient water is added to the materials in the vials to form a solution containing 100mg. of active ingredient per milliliter of injectable solution.

EXAMPLE 25

Suspension

A suspension of 1-[3-(4-methyl-1-piperazinyl)propyl]-2-(3-trifluoromethylbenzamido)-5-trifluoromethylbenzimidazole hemihydrate is prepared with the following composition:

| Effective ingredient | g. | 25.00 |
|---|---|---|
| 70% aqueous sorbitol | g. | 741.29 |
| Glycerine, U.S.P. | g. | 185.35 |
| Gum acacia (10% solution) | ml. | 100.00 |
| Polyvinylpyrrolidone | g. | 0.50 |
| Distilled water, sufficient to make 1 liter. | | |

To this suspension, various sweeteners and flavorants are added to improve the palatability of the suspension. The suspension contains approximately 25 mg. of effective agent per milliliter.

EXAMPLE 26

Solid Dispersion

A solid dispersion containing 20% 2-(3-trifluoromethylbenzamido)-3-[3-(4-methyl-1-piperazino)propyl]-imidazo[4,5-b]pyridine hydrate and 80% polyethylene glycol 6000 (PEG 6000) is prepared by adding in small portions and with constant stirring 100 g. of the effective ingredient to 500 g. of PEG 6000 heated to 70° C. When all the compound is added, the melt is "flash cooled" by cooling in an ice bath and the solidified product reduced to a fine powder and passed through a 100 mesh sieve. The material not passing through is recycled through the melting process.

EXAMPLE 27

The adjuvant arthritis screen as described by Walz et al. (*Ann. Rheum Dis.*, 30: 303 (1971), was used to evaluate the above prepared compounds.

The screen is conducted using male inbred Lewis rats weighing approximately 250 gm. The animals are dosed with drug beginning on day -1 and continuing daily through day 15. On Day 0, the subplanter surface of the right hind paw is injected with 0.1cc of a 1% suspension of Mycobacterium butyricum (Freunds adjuvant) in Primol (Esso). The swelling of the non-injected left hind foot on Day 16, resulting from immune response to adjuvant, was determined for dosed animals and controls. The foot volume is measured by immersing the paw to the anatomical hairline into a mercury reservoir which is connected to a Statham pressure transducer and a recording device. The results are expressed as % inhibition calculated according to the following equation:

$$\frac{\text{Mean increase in foot volume (Control)} - \text{increase in foot volume (test)}}{\text{Mean increase in foot volume (Control)}} \times 100 = \% \text{ inhibition}$$

The results obtained are as follows for

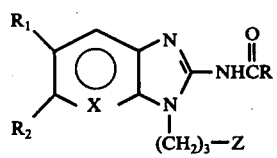

where Z is —N(CH$_3$)$_2$ and X is carbon:

| | | | Activity | | |
|---|---|---|---|---|---|
| R | R$_1$ | R$_2$ | Percent Inhibition | Dose, mg./kg. | *Route of Administration |
| 3-Trifluoromethylphenyl | H | H | 21 | 33 | ip |
| 4-Methoxyphenyl | H | H | 59 | 33 | ip |
| | | | 12 | 10 | po |
| 3-Methoxyphenyl | H | H | 21 | 33 | ip |
| 4-Chlorophenyl | H | H | 51 | 33 | ip |
| | | | 27 | 10 | ip |
| 3-Chlorophenyl | H | H | 33 | 33 | ip |
| 3,4-Dichlorophenyl | H | H | 67 | 33 | ip |
| | | | 13 | 10 | po |
| CH$_3$OCH$_2$— | H | H | 32 | 33 | ip |
| 2-Chlorostyryl | H | H | 45 | 33 | ip |
| 4-Chlorostyryl | H | H | 33 | 33 | ip |
| 3-Methylphenyl | H | H | 21 | 33 | ip |
| Phenyl | H | H | 8 | 33 | ip |
| 2-Chlorophenyl | H | H | 15 | 33 | ip | and where Z is —N⟨O⟩ and X is carbon:

| 3-Chlorophenyl | H | H | 32 | 100 | po |
| 4-Chlorophenyl | H | H | 15 | 33 | ip |
| 4-Methoxyphenyl | H | H | 54 | 33 | ip |
| 3-Methoxyphenyl | H | H | 29 | 33 | ip |
| 3-Trifluoromethylphenyl | H | H | 0 | 33 | ip |

-continued

| R | $R_1$ | $R_2$ | Activity Percent Inhibition | Dose, mg./kg. | *Route of Administration |
|---|---|---|---|---|---|
| 3-Methylphenyl | H | H | 40 | 33 | ip |
| $CH_3OCH_2-$ | H | H | 21 | 33 | ip |
| $(CH_3)_3CCH_2-$ | H | H | 13 | 33 | ip |
| Phenyl | H | H | 15 | 33 | ip |
| 4-Trifluoromethylphenyl | H | H | 35 | 33 | ip |
| 2-Fluorophenyl | H | H | 6 | 33 | ip | and where Z is , X is carbon:

| 3-Trifluoromethylphenyl | H | H | 79 | 33 | ip |
|---|---|---|---|---|---|
|  |  |  | 18 | 10 | po |
| 4-Trifluoromethylphenyl | H | H | 77 | 33 | ip |
|  |  |  | 51 | 20 | po |
| 2-Furyl | H | H | 43 | 20 | po |
| 4-Chlorophenyl | H | H | 43 | 33 | ip |
| 3-Chlorophenyl | H | H | 46 | 33 | ip |
| 3,4-Dichlorophenyl | H | H | 61 | 33 | ip |
|  |  |  | 32 | 10 | po |
| 3-Methoxyphenyl | H | H | 26 | 33 | ip |
| 4-Methoxyphenyl | H | H | 27 | 33 | ip |
| 3-Methylphenyl | H | H | 39 | 33 | ip |
| $CH_3(CH_2)_8$ | H | H | 45 | 20 | po |
| Cyclobutyl | H | H | 34 | 33 | ip |
| 1-Adamantyl | H | H | 28 | 33 | ip |
| p-Phenylphenyl | H | H | 46 | 33 | ip |
| 3,5-Dichlorophenyl | H | H | 31 | 33 | ip |
| 3,5-bis-Trifluoromethylphenyl | H | H | 32 | 20 | po |
| 4-t-Butylphenyl | H | H | 26 | 33 | ip |
| 3-Fluorophenyl | H | H | 34 | 33 | ip |
| 4-Trifluoromethylphenyl | $CF_3$ | H | 71 | 33 | ip |
|  |  |  | 28 | 10 | po |
| 3-Trifluoromethylphenyl | $CF_3$ | H | 83 | 33 | ip |
|  |  |  | 46 | 10 | po |
| 3-Chlorophenyl | $CF_3$ | H | 73 | 33 | ip |
|  |  |  | 45 | 20 | po |
| 4-Chlorostyryl | $CF_3$ | H | 6 | 20 | po |
| 4-Chlorophenyl | $CF_3$ | H | 47 | 33 | ip |
| 3-Methoxyphenyl | $CF_3$ | H | 46 | 33 | ip |
| Phenyl | $CF_3$ | H | 29 | 33 | ip |
| 4-Trifluoromethylphenyl | Cl | H | 72 | 33 | ip |
|  |  |  | 38 | 10 | po |
| 3-Trifluoromethylphenyl | Cl | H | 74 | 33 | ip |
|  |  |  | 16 | 10 | po |
| 4-Chlorophenyl | Cl | H | 63 | 33 | ip |
|  |  |  | −10 | 10 | po |
| 3-Chlorophenyl | Cl | H | 66 | 33 | ip |
|  |  |  | −5 | 10 | po |
| 4-Methoxyphenyl | Cl | H | 46 | 33 | ip |
| 3-Methoxyphenyl | Cl | H | 17 | 33 | ip |
| 4-Chlorostyryl | Cl | H | 66 | 33 | ip |
| Phenyl | Cl | H | 41 | 33 | ip |
| Phenyl | H | $CH_3$ | 23 | 20 | po |
| 3-Methoxyphenyl | H | $CH_3$ | 44 | 20 | po |
| 4-Methoxyphenyl | H | $CH_3$ | 22 | 20 | po |
| 4-Trifluoromethylphenyl | H | $CH_3$ | 50 | 20 | po |
| 3-Chlorophenyl | H | $CH_3$ | 66 | 33 | ip |
|  |  |  | −5 | 10 | po |
| 3-Trifluoromethylphenyl | H | $CH_3$ | 21 | 20 | po |
| 3,4-Dichlorophenyl | H | $CH_3$ | 22 | 20 | po |
| Phenyl | $CH_3$ | $CH_3$ | 31 | 20 | po |
| 3-Trifluoromethylphenyl | $CH_3$ | $CH_3$ | 22 | 20 | po |
| 4-Trifluoromethylphenyl | $CH_3$ | $CH_3$ | 29 | 20 | po |
| 4-Chlorophenyl | $CH_3$ | $CH_3$ | 30 | 20 | po |
| 3,4-Dichlorophenyl | $CH_3$ | $CH_3$ | 18 | 20 | po |
| 3-Trifluoromethylphenyl | Cl | Cl | 74 | 33 | ip |
| 3-Chlorophenyl | Cl | Cl | 66 | 33 | ip |
| 4-Chlorostyryl | $CH_3$ | H | 39 | 20 | po |
| 3-Methoxyphenyl | $CH_3$ | H | 37 | 20 | po |
| 4-Chlorophenyl | $CH_3$ | H | 27 | 20 | po |
| 3-Chlorophenyl | $CH_3$ | H | 29 | 20 | po |
| 4-Trifluoromethylphenyl | $CH_3$ | H | 35 | 20 | po |
| 3-Trifluoromethylphenyl | $CH_3$ | H | 27 | 20 | po |
| Phenyl | $OCH_3$ | H | 27 | 33 | ip |
| 3-Chlorophenyl | $OCH_3$ | H | 59 | 33 | ip |
|  |  |  | −1 | 10 | po |
| 3-Methoxyphenyl | $OCH_3$ | H | 43 | 33 | ip |
| 4-Trifluoromethylphenyl | $OCH_3$ | H | 69 | 33 | ip |
| 3-Trifluoromethylphenyl | $OCH_3$ | H | 57 | 33 | ip |
|  |  |  | −5 | 10 | po |
| 4-Chlorostyryl | $OCH_3$ | H | 47 | 10 | po |
| 3,4-Dichlorophenyl | $OCH_3$ | H | 35 | 10 | po |
| Phenyl | $-SO_2N(CH_3)_2$ | H | 32 | 20 | po |
| 4-Methoxyphenyl | $-SO_2N(CH_3)_2$ | H | 27 | 20 | po |
| 3-Trifluoromethylphenyl | $-SO_2N(CH_3)_2$ | H | 22 | 20 | po |
| 4-Trifluoromethylphenyl | $-SO_2N(CH_3)_2$ | H | 34 | 20 | po |
| 3,4-Dichlorophenyl | $-SO_2N(CH_3)_2$ | H | 31 | 20 | po |
| 3-Chlorophenyl | $-SO_2N(CH_3)_2$ | H | 54 | 33 | po |
|  |  |  | 35 | 10 | po |
| 4-Chlorophenyl | $-SO_2N(CH_3)_2$ | H | 18 | 20 | po |

-continued

| R | R₁ | R₂ | Percent Inhibition | Dose, mg./kg. | *Route of Administration |
|---|---|---|---|---|---|
| 3-Methoxyphenyl | —SO₂N(CH₃)₂ | H | 13 | 20 | po | and where Z is —N⟨ ⟩N—CH₃ and X is nitrogen;

| | | | | | |
|---|---|---|---|---|---|
| 4-Trifluoromethylphenyl | H | H | 14 | 20 | po |
| 3-Trifluoromethylphenyl | H | H | 39 | 20 | po |
| 3,4-Dichlorophenyl | H | H | 41 | 20 | po |
| | | | 27 | 10 | po |
| 3-Methoxyphenyl | H | H | 25 | 20 | po |
| 4-Chlorophenyl | H | H | 26 | 20 | po |
| 3-Chlorophenyl | H | H | 26 | 20 | po |
| 4-Methoxyphenyl | H | H | 5 | 20 | po | and where Z is —N⟨ ⟩ and X is carbon:

| | | | | | |
|---|---|---|---|---|---|
| 4-Trifluoromethylphenyl | H | H | 79 | 33 | ip |
| 4-Chlorophenyl | H | H | 46 | 33 | ip |
| 3-Chlorophenyl | H | H | 34 | 33 | ip |
| 3,4-Dichlorophenyl | H | H | 25 | 33 | ip |
| 3-Fluorophenyl | H | H | 27 | 33 | ip |
| 3-Trifluoromethylphenyl | H | H | 30 | 33 | ip |
| 3-Methoxyphenyl | H | H | 52 | 33 | ip |
| Styryl | H | H | 33 | 33 | ip |
| Furyl | H | H | 12 | 33 | ip | and where Z is —N⟨ ⟩N—CH₂—⟨phenyl⟩ and X is carbon:

| | | | | | |
|---|---|---|---|---|---|
| Phenyl | H | H | 44 | 10 | ip |
| 4-Trifluoromethylphenyl | H | H | 47 | 10 | ip |
| 3-Trifluoromethylphenyl | H | H | 35 | 10 | ip |
| 4-Methoxyphenyl | H | H | 32 | 10 | ip |
| 3,4-Dichlorophenyl | H | H | 19 | 10 | ip | and where Z is —N⟨ ⟩NH and X is carbon:

| | | | | | |
|---|---|---|---|---|---|
| Phenyl | H | H | 19 | 10 | ip |
| 4-Trifluoromethylphenyl | H | H | 28 | 10 | ip |
| 3-Trifluoromethylphenyl | H | H | 13 | 10 | po |

*ip, Intraperitoneal
po, Oral (per os)

Preparation A a. 4-Chloro-3-nitrobenzenesulfonyl chloride

Under a nitrogen atmosphere, 350 ml. of chlorosulfonic acid was added to 236 g. (1.50 mole) of 2-chloronitrobenzene. The resulting green colored solution was heated for 18 hours at 80° C., then the temperature was increased to 140° C. and held at this temperature until HCl gas evolution ceased (about 90 minutes). The reaction mixture was then cooled to 25° C. and slowly poured onto 4 liters of ice. After stirring for 20 minutes the mixture was filtered to obtain a pale yellow solid. The filter cake was sucked dry then allowed to dry in a vacuum oven at 25° C. overnight, m.p. 37°–38° C., yield 362.3 g. (94%).

b. 4-Chloro-3-nitro-N,N-dimethylbenzenesulfonamide

A solution of 2-chloro-3-nitrobenzenesulfonyl chloride (352.3 g., 1.38 moles) in 1000 ml. of methanol was stirred under nitrgen while cooling in an ice bath to 5° C. To this was then added dropwise over one hour 666 ml. of 3.33 molar dimethylamine in methanol. The temperature did not exceed 12° C. during the addition. The resulting mixture was then stirred at 5°–10° C. for 15 minutes, poured into 3 liters of water and stirred for 30 minutes. The green solid which precipitated was recovered by filtration and dried in a vacuum oven at 25° C. Recrystallization from 1500 ml. of ethyl ether gave 192.7 g. (52%) of large yellow crystals in three crops, m.p. 97°–100° C.

What is claimed is:

1. A compound having the formula:

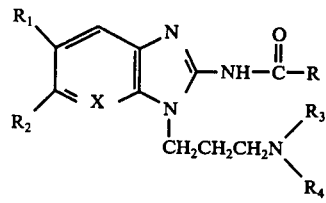

and the pharmaceutically acceptable acid addition salts thereof wherein R is styryl, chlorostyryl, phenyl, or mono- or disubstituted phenyl wherein each substituent is chloro, bromo, fluoro, trifluoromethyl, phenyl, alkoxy or alkyl, said alkoxy or alkyl having from 1 to 4 carbon atoms; $R_1$ and $R_2$ are each hydrogen, chloro, bromo, fluoro, trifluoromethyl, methoxy or methyl; X is nitrogen; and $R_3$ and $R_4$ when taken separately are each alkyl having from 1 to 4 carbon atoms and when taken together with the nitrogen to which they are attached form piperidino, pyrrolidino, morpholino, piperazino, 4-benzylpiperazino or 4-alkylpiperazino, said alkyl having from 1 to 4 carbon atoms.

2. The compound of claim 1 wherein $R_3$ and $R_4$ when taken together with the nitrogen to which they are attached form a 4-methyl piperazino ring.

3. The compound of claim 2 wherein $R_1$ and $R_2$ are each hydrogen and R is 3-trifluoromethylphenyl.

4. The compound of claim 2, wherein $R_1$ and $R_2$ are each hydrogen and R is 3,4-dichlorophenyl.

5. A compound of claim 1 wherein R is monosubstituted phenyl wherein each substituent is chloro, trifluoromethyl or methoxy, disubstituted phenyl wherein each substitutent is chloro; $R_1$ and $R_2$ are each hydrogen; and $R_3$ and $R_4$ taken together with the nitrogen to which they are attached form a 4-alkylpiperazino ring said alkyl having from 1 to 4 carbon atoms.

* * * * *